(12) United States Patent
Hoshino et al.

(10) Patent No.: US 9,738,789 B2
(45) Date of Patent: Aug. 22, 2017

(54) METHOD FOR PRODUCING SILICON COMPOUND

(71) Applicant: Asahi Glass Company, Limited, Chiyoda-ku (JP)

(72) Inventors: Taiki Hoshino, Chiyoda-ku (JP); Eisuke Murotani, Chiyoda-ku (JP); Akira Isobe, Chiyoda-ku (JP)

(73) Assignee: Asahi Glass Company, Limited, Chiyoda-ku (JP)

( * ) Notice: Subject to any disclaimer, the term of this patent is extended or adjusted under 35 U.S.C. 154(b) by 0 days.

(21) Appl. No.: 15/162,908

(22) Filed: May 24, 2016

(65) Prior Publication Data

US 2016/0264600 A1 Sep. 15, 2016

Related U.S. Application Data

(63) Continuation of application No. PCT/JP2014/082650, filed on Dec. 10, 2014.

(30) Foreign Application Priority Data

Dec. 13, 2013 (JP) .................. 2013-258414
Dec. 13, 2013 (JP) .................. 2013-258415

(51) Int. Cl.
| | | |
|---|---|---|
| *C09D 4/00* | (2006.01) |
| *C09D 7/12* | (2006.01) |
| *C09D 171/02* | (2006.01) |
| *C08G 65/336* | (2006.01) |
| *C08L 71/02* | (2006.01) |
| *C08G 65/00* | (2006.01) |
| *C04B 41/82* | (2006.01) |
| *C23C 16/56* | (2006.01) |
| *C07F 7/08* | (2006.01) |

(52) U.S. Cl.
CPC ............... *C09D 4/00* (2013.01); *C04B 41/82* (2013.01); *C07F 7/0818* (2013.01); *C07F 7/0829* (2013.01); *C08G 65/007* (2013.01); *C08G 65/336* (2013.01); *C08L 71/02* (2013.01); *C09D 7/12* (2013.01); *C09D 171/02* (2013.01); *C23C 16/56* (2013.01)

(58) Field of Classification Search
CPC ......... C08G 65/336; C07B 61/00; C07F 7/18; C09K 3/18
USPC ............................................. 556/445; 528/15
See application file for complete search history.

(56) References Cited

U.S. PATENT DOCUMENTS

| | | |
|---|---|---|
| 6,191,297 B1 | 2/2001 | Batz-Sohn et al. |
| 6,303,728 B1 * | 10/2001 | Hagimori .................. C08F 8/42 528/15 |
| 2002/0013427 A1 | 1/2002 | Tsuji et al. |
| 2006/0217513 A1 | 9/2006 | Asai et al. |
| 2011/0098435 A1 | 4/2011 | Hofmann et al. |
| 2012/0328863 A1 | 12/2012 | Kuo |
| 2014/0202355 A1 | 7/2014 | Hoshino |
| 2014/0287240 A1 | 9/2014 | Murotani et al. |
| 2014/0287246 A1 | 9/2014 | Murotani et al. |
| 2014/0302332 A1 | 10/2014 | Murotani et al. |
| 2016/0009929 A1 | 1/2016 | Hoshino et al. |

FOREIGN PATENT DOCUMENTS

| | | |
|---|---|---|
| EP | 1 018 530 A2 | 7/2000 |
| JP | 4-117390 | 4/1992 |
| JP | 7-91389 | 10/1995 |
| JP | 11-80167 | 3/1999 |
| JP | 2000-26478 | 1/2000 |
| JP | 2001-294659 | 10/2001 |
| JP | 2006-299237 | 11/2006 |
| JP | 2011-522935 | 8/2011 |
| JP | 2012-102187 | 5/2012 |
| WO | WO 03/014129 A1 | 2/2003 |
| WO | WO 2009/008380 A1 | 1/2009 |
| WO | WO 2011/087146 A1 | 7/2011 |
| WO | WO 2013/042732 A1 | 3/2013 |
| WO | WO 2013/121986 A1 | 8/2013 |

OTHER PUBLICATIONS

International Search Report issued Mar. 24, 2015 in PCT/JP2014/082650 filed on Dec. 10, 2014.
U. Mayer, "Ionic Equilibria in Donor Solvents", Pure & Appl. Chem., vol. 41, (3), 1975, 36 pgs.
Ingmar Persson, "Solvation and complex formation in strongly solvating solvents", Pure & Appl. Chem., vol. 58, (8), 1986, 9 pgs.

* cited by examiner

*Primary Examiner* — Sudhakar Katakam
*Assistant Examiner* — Kofi Adzamli
(74) *Attorney, Agent, or Firm* — Oblon, McClelland, Maier & Neustadt, L.L.P.

(57) ABSTRACT

To provide a method for producing a silicon compound, whereby a hydrosilylation reaction of a compound having a 2-propenyl group, can be conducted with high selectivity by a simple and easy method. The method for producing a silicon compound comprises reacting a compound (3) having a group represented by —$CH_2CH$=$CH_2$ and a silicon compound (4) having an H—Si bond in the presence of a transition metal catalyst (C) and a compound (D) having a group represented by —S(=O)— to obtain a compound (5) having a group represented by —$CH_2CH_2CH_2Si$≡.

15 Claims, No Drawings

METHOD FOR PRODUCING SILICON COMPOUND

This application is a continuation of PCT Application No. PCT/JP2014/082650, filed on Dec. 10, 2014, which is based upon and claims the benefit of priorities from Japanese Patent Application No. 2013-258414 filed on Dec. 13, 2013 and Japanese Patent Application No. 2013-258415 filed on Dec. 13, 2013. The contents of those applications are incorporated herein by reference in their entireties.

TECHNICAL FIELD

The present invention relates to a method for producing a silicon compound.

BACKGROUND ART

A compound having a hydrolyzable silyl group at its terminal is likely to undergo an intermolecular reaction or to form a chemical bond with the surface of a substrate. Therefore, such a compound is widely used as a surface treatment agent or a reactive adhesive. For example, by coating a substrate with a compound having a hydrolyzable silyl group introduced at a terminal of its molecule having a specific function, it is possible to bond the molecule having a specific function to the surface of the substrate.

As a method for introducing a hydrolyzable silyl group at a terminal, a method is preferably used wherein at a terminal of the molecule of a starting compound, a 2-propenyl group (—CH$_2$CH═CH$_2$, common name: allyl group) is introduced, and then, to the compound having the 2-propenyl group introduced, a hydrosilane compound is reacted for hydrosilylation. The hydrosilylation reaction may, for example, be carried out in the presence of a very small amount of a transition metal catalyst.

The method for introducing a 2-propenyl group at a terminal of the molecule of a starting compound, may, for example, be a method wherein a compound having a 3-halopropyl group at a terminal of its molecule is dehydrohalogenated to convert the terminal to a 2-propenyl group, or a method wherein a compound having a hydroxy group at a terminal of its molecule is reacted with an allyl halide to obtain an allyl ether compound having an allyloxy group (—O—CH$_2$CH═CH$_2$) at the terminal of its molecule.

However, the selectivity of the hydrosilylation reaction is not necessarily high depending on the type of the compound having a 2-propenyl group at a terminal of its molecule. For example, according to a hydrosilylation reaction of an allyl ether compound, the desired compound having a hydrolyzable silyl group at a terminal may be formed from 75 to 85 mol %, but at the same time, a by-product having a 1-propenyl group (—CH═CH—CH$_3$) with the double bond moved to the inside would be formed from 15 to 25 mol % by a side reaction.

If the formation of such a by-product is high, the production cost for the desired compound tends to increase. Further, an additional process step of separating the compound and the by-product will be required. In general, in the case of a reaction of a compound with a low molecular weight, the boiling point of a desired compound becomes sufficiently higher than the boiling points of the starting material and by-product, and thus, they can easily be separated by distillation purification. However, if the starting material is a compound with a high molecular weight, the separation by distillation purification itself tends to be difficult, and it will be obliged to use the reaction mixture containing the desired compound and by-product, as it is, as a surface treatment agent, etc. In that case, if the by-product in the reaction mixture is substantial, the adhesion between the surface treatment agent and the substrate tends to be low, and the function as a surface treatment agent tends to be inadequate.

Further, for example, propenyl ether as a by-product having a 1-propenyl group, will, when reacted with water, form propionaldehyde which causes bad odor (see Patent Document 1).

PRIOR ART DOCUMENT

Patent Document

Patent Document JP-B-7-91389

DISCLOSURE OF INVENTION

Technical Problem

It is an object of the present invention to provide a method for producing a silicon compound, whereby a hydrosilylation reaction of a compound having a 2-propenyl group can be conducted with high selectivity by a simple and easy method.

Solution to Problem

The present invention provides a method for producing a silicon compound, having the following constructions [1] to [11].

[1] A method for producing a silicon compound, characterized by reacting a compound having a group represented by the following formula (3) and a silicon compound (4) having an H—Si bond in the presence of a transition metal catalyst (C) and a compound having a group represented by the following formula (D) to obtain a compound having a group represented by the following formula (5):

—CH$_2$CH═CH$_2$    (3)

—S(═O)—    (D)

—CH$_2$CH$_2$CH$_2$Si≡    (5)

[2] The method for producing a silicon compound according to [1], wherein the compound having a group represented by the above formula (D) is dimethyl sulfoxide or tetramethylene sulfoxide.

[3] The method for producing a silicon compound according to [1] or [2], wherein the silicon compound (4) having an H—Si bond is a compound represented by the following formula (41), and the group represented by the formula (5) is a group represented by the following formula (5-1):

HSiL$_m$R$_n$    (41)

—CH$_2$CH$_2$CH$_2$SiL$_m$R$_n$    (5-1)

the symbols in the formulae represent the following:
L: a hydrolyzable group,
R: a monovalent hydrocarbon group,
m and n: m is an integer of from 1 to 3, and n is an integer of from 0 to 2, provided m+n=3.

[4] The method for producing a silicon compound according to [3], wherein L is a C$_{1-4}$ alkoxy group.

[5] The method for producing a silicon compound according to [1] or [2], wherein the silicon compound (4) having an H—Si bond is a linear or cyclic organopolysiloxane compound.

[6] The method for producing a silicon compound according to any one of [1] to [5], wherein the compound having a group represented by the above formula (3) is a compound having an allyloxy group.

[7] The method for producing a silicon compound according to any one of [1] to [6], wherein the compound having a group represented by the above formula (3) is a compound having from 1 to 3 groups represented by the above formula (3).

[8] The method for producing a silicon compound according to any one of [1] to [7], wherein the compound having a group represented by the above formula (3) is a compound having a polyoxyalkylene chain or a polyoxyfluoroalkylene chain.

[9] The method for producing a silicon compound according to any one of [1] to [8], wherein the number average molecular weight of the compound having a group represented by the above formula (3) is from 200 to 20,000.

[10] The method for producing a silicon compound according to any one of [1] to [9], wherein the transition metal catalyst (C) is a platinum catalyst.

[11] The method for producing a silicon compound according to [10], wherein the transition metal catalyst (C) is a Pt/divinyltetramethyldisiloxane complex or a Pt/tetramethyltetravinylcyclotetrasiloxane complex.

Advantageous Effect of Invention

According to the method for producing a silicon compound of the present invention, a hydrosilylation reaction of a compound having a 2-propenyl group can be conducted with high selectivity by a simple and easy method.

DESCRIPTION OF EMBODIMENTS

In this specification, a compound represented by the formula (41) will be referred to as compound (41). Compounds represented by other formulae will be referred to in the same manner. Further, a group represented by the formula (D) will be referred to as group (D). Groups represented by other formulae will be referred to in the same manner. Further, a compound having a group represented by the formula (3) will be referred to as compound (3). Compounds having groups represented by other formulae will be referred to in the same manner.

The following definitions of terms apply throughout this specification including claims.

A "hydrolyzable silyl group" means a group capable of forming a silanol group (Si—OH) by hydrolysis. For example, -SiL$_m$R$_n$ in the formula (41) is a hydrolyzable silyl group.

An "etheric oxygen atom" means an oxygen atom to form an ether bond (—O—) between carbon-carbon atoms.

A "fluoroalkylene group" means a group having some or all of hydrogen atoms in an alkylene group substituted by fluorine atoms, and a "perfluoroalkylene group" means a group having all of hydrogen atoms in an alkylene group are substituted by fluorine atoms.

A "fluoroalkyl group" means a group having some or all of hydrogen atoms in an alkyl group substituted by fluorine atoms, and a "perfluoroalkyl group" means a group having all of hydrogen atoms in an alkyl group substituted by fluorine atoms.

The chemical formula of an oxyperfluoroalkylene group shall be presented to show the oxygen atom on the right-hand side of a perfluoroalkylene group. The same applies to the chemical formula of an oxyalkylene group.

An "organic group" means a group having carbon atom(s).

[Compound (3)]

Compound (3) has at least one group represented by the following formula (3) (i.e. 2-propenyl group). The number of groups (3) which compound (3) may have, is not particularly limited, and may be determined depending upon e.g. efficiency in preparation of compound (3), the reactivity with a silicon compound (4) having an H—Si bond (hereinafter referred to also as "compound (4)") and the application of compound (5) to be prepared by the method of the present invention. In the case of using compound (5) as a surface treatment agent, from the viewpoint of high surface modification properties, the number of groups (3) which compound (3) has, is preferably at most 3, particularly preferably at most 2. In the case of using it as a reactive adhesive, from such a viewpoint that sufficient adhesion can be imparted, the number of groups (3) which compound (3) has, is preferably at least 2, particularly preferably at least 3. One of compounds (3) may be used alone or two or more of them may be used in combination.

—CH$_2$CH=CH$_2$ (3)

Compound (3) having one group (3) is represented by the following formula (3A), and compound (3) having two groups (3) is represented by the following formula (3B).

R$^A$—CH$_2$CH=CH$_2$ (3A)

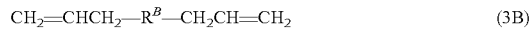
CH$_2$=CHCH$_2$—R$^B$—CH$_2$CH=CH$_2$ (3B)

Compound (3) having three groups (3) is represented by the following formula (3C).

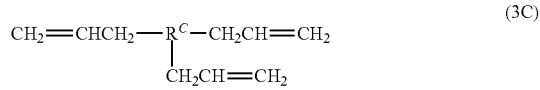
$$\begin{array}{c} CH_2=CHCH_2-R^C-CH_2CH=CH_2 \\ | \\ CH_2CH=CH_2 \end{array} \quad (3C)$$

Of R$^A$, R$^B$ and R$^C$ in the above formulae, the terminal bonded to group (3) is preferably an etheric oxygen atom. That is, compound (3) is preferably a compound having an allyloxy group. Likewise, in a case where the number of groups (3) in compound (3) is 4 or more, compound (3) is preferably a compound having 4 or more allyloxy groups.

(Compound (3A))

Compound (3A) has one group (3), and therefore, by a reaction of compound (3A) with compound (4), a compound having one group (5) will be formed. For example, in the case of using, as compound (4), a compound represented by the following formula (41), a compound represented by the following formula (5-11) will be formed.

HSiL$_m$R$_n$ (41)

R$^A$—CH$_2$CH$_2$CH$_2$SiL$_m$R$_n$ (5-11)

The symbols in the formulae represent the following:

L: a hydrolyzable group,
R: a monovalent hydrocarbon group,
m and n: m is an integer of from 1 to 3, and n is an integer of from 0 to 2, provided m+n=3.

R$^A$ in the formula (3A) is an atom or a monovalent group linked with —CH$_2$CH=CH$_2$, and may, for example, be a hydrogen atom, a halogen atom, an amino group or a monovalent organic group.

The halogen atom may, for example, be a fluorine atom, a chlorine atom, a bromine atom or an iodine atom.

The monovalent organic group may, for example, be an alkyl group, an alkenyl group, an alkynyl group, an aryl group, an aralkyl group or a heterocyclic group. The alkyl, alkenyl and alkynyl groups may have at least one member selected from the group consisting of —O—, —S—, —CO—O—, —CO—S—, —CO—NH— and —NH—CO—O—, between carbon-carbon atoms or at their terminal(s). Further, the monovalent organic group may be a halogenated organic group having some or all of hydrogen atoms bonded to its carbon atoms substituted by halogen atoms.

In a case where $R^A$ is a monovalent organic group, as mentioned above, its bonding terminal is preferably an etheric oxygen atom. Further, $R^A$ preferably has a polyoxyalkylene chain or a polyoxyfluoroalkylene chain. The polyoxyfluoroalkylene chain may be a polyoxyperfluoroalkylene chain.

Compound (3) having a polyoxyalkylene chain or a polyoxyfluoroalkylene chain tends to be a relatively high molecular weight compound in many cases, and as will be described below, the present invention is suitable as a method for producing a compound (5) from such a relatively high molecular weight compound (3).

As $R^A$, preferred are $CH_3$—$R^{41}$—O—, $CH_3$—$R^{41}$—O—$(C_yH_{2y}O)_{y1}$—, $CH_3$—$R^{41}$—, $CF_3$—$R^{41}$—O—, $CF_3$—$R^{41}$—O—$(C_yH_{2y}O)_{y1}$—, $CF_3$—$R^{41}$—O—$(C_oF_{2o}O)_{o1}$—, $CF_3$—$R^{41}$— and groups represented by the following formulae:

$R^{41}$ is a single bond or a $C_{1-30}$ alkylene or fluoroalkylene group, and the number of carbon atoms in the alkylene or fluoroalkylene group is preferably from 1 to 20. Each of y and σ is an integer of from 1 to 10, preferably from 1 to 4. Each of y1 and σ1 is an integer of from 1 to 500, preferably from 1 to 200.

The alkylene or fluoroalkylene group may be either linear or branched.

When y1 is at least 2, $(C_yH_{2y}O)_{y1}$ may be composed of at least two types of $C_yH_{2y}O$ different in y. Specific examples of $(C_yH_{2y}O)$ include an oxyethylene group, an oxypropylene group, an oxytrimethylene group, an oxytetramethylene group, etc.

When σ1 is at least 2, $(C_oF_{2o}O)_{o1}$ may be composed of at least two types of $C_oF_{2o}O$ different in σ.

As $R^A$, also a group represented by the following formula (1) is preferred.

The symbols in the formula (1) represent the following:
A: a $C_{1-20}$ perfluoroalkyl group,
Q: a single bond, —$CH_2$—, —CHF—, -$Q^1$-$CH_2$—, -$Q^1$-CHF—, -$Q^1$-O—$CH_2$—, -$Q^1$-O—CHF—, -$Q^1$-$CH_2$—O— or -$Q^1$-CHF—O—,
$Q^1$: a $C_{1-10}$ fluoroalkylene group, a $C_{2-10}$ fluoroalkylene group having an etheric oxygen atom between carbon-carbon atoms, a $C_{1-10}$ alkylene group, or a $C_{2-10}$ alkylene group having an etheric oxygen atom between carbon-carbon atoms,
b, d: b is an integer of from 1 to 10, and d is an integer of from 1 to 200, provided that when d is at least 2, $(C_bF_{2b}O)_d$ may be composed of at least 2 types of $C_bF_{2b}O$ different in b.

X: a divalent organic group having no $CF_2O$.

Compound (5-11) (hereinafter referred to also as "compound (5-11a)") obtained by reacting compound (3A) wherein RA is group (1) (hereinafter referred to also as "compound (3A1)") and compound (41), is useful as a surface treatment agent for forming a surface-treated layer having water/oil repellency on the surface of a substrate, such as a member constituting a surface of, for example, a touch panel to be touch by a finger.

Here, compound (3A1) may be a mixture of at least two compounds different in at least one of A, Q, $(C_bF_{2b}O)_d$ and X.

<Group A>

Group A is a $C_{1-20}$ perfluoroalkyl group. As the $C_{1-20}$ perfluoroalkyl group, from such a viewpoint that when compound (5-11a) is used as a surface treatment agent, it is possible to form a surface-treated layer which is more excellent in abrasion resistance whereby water and oil repellency is less likely to be lowered even by repeated abrasion, a $C_{1-6}$ perfluoroalkyl group is preferred, and a $C_{1-3}$ perfluoroalkyl group is particularly preferred. The perfluoroalkyl group may be either linear or branched, and may have a substituent group containing a ring structure.

As A, $CF_3$—, $CF_3CF_2$—, $CF_3CF_2CF_2$—, $CF_3CF_2CF_2CF_2$—, $CF_3CF_2CF_2CF_2CF_2$— or $CF_3CF_2CF_2CF_2CF_2CF_2$— is preferred, and $CF_3$—, $CF_3CF_2$— or $CF_3CF_2CF_2$— is particularly preferred.

<Group Q>

Group Q is a single bond, —$CH_2$—, —CHF—, -$Q^1$-$CH_2$—, -$Q^1$-CHF—, -$Q^1$-O—$H_2$—, -$Q^1$-O—CHF—, -$Q^1$-$CH_2$—O— or -$Q^1$-CHF—O—, and $Q^1$ is a $C_{1-10}$ fluoroalkylene group, a $C_{2-10}$ fluoroalkylene group having an etheric oxygen atom between carbon-carbon atoms, a $C_{1-10}$ alkylene group, or a $C_{2-10}$ alkylene group having an etheric oxygen atom between carbon-carbon atoms.

The fluoroalkylene group may be a perfluoroalkylene group or a fluoroalkylene group having at least one hydrogen atom. A perfluoroalkylene group is preferred from such a viewpoint that when compound (5-11a) is used as a surface treatment agent, water/oil repellency of the surface-treated layer to be formed will be superior. A fluoroalkylene group having at least one hydrogen atom is preferred from such a viewpoint that the solubility of compound (5-11a) in a solvent will be excellent, aggregation of compound (5-11a) in a coating liquid or at the time of application to the surface of a substrate to form a surface-treated layer, is suppressed, and it is possible to form a surface-treated layer excellent in uniformity.

As group Q, from the viewpoint of e.g. production efficiency of compound (3A1), a single bond, —$CH_2$—, -$Q^1$-$CH_2$— or -$Q^1$-O—$CH_2$— is preferred.

$Q^1$ preferably has from 1 to 8 carbon atoms. As $Q^1$ in -$Q^1$-$CH_2$—, for example, —$CF_2$—, —$CF_2CF_2OCF_2$— or —$CF_2CF_2OCF_2CF_2OCF_2$— is preferred. As $Q^1$ in -$Q^1$-O—$CH_2$—, —$CHFCF_2$—, —$CF_2CF_2$—O—$CHFCF_2$—, —$CF_2CF_2OCF_2CF_2$—O—$CHFCF_2$—, —$CF(CF_3)CF_2$—O—$CHFCF_2$— or —$CF(CF_3)CF_2OCF(CF_3)CF_2$—O—$CHFCF_2$— is preferred. Among them, from the viewpoint of abrasion resistance, as $Q^1$, —$CF_2$— or linear $Q^1$ is preferred, and as linear $Q^1$, —$CHFCF_2$—, —$CF_2CF_2$—O—$CHFCF_2$—, —$CF_2CF_2OCF_2CF_2$—O—$CHFCF_2$—, —$CF_2CF_2OCF_2$— or —$CF_2CF_2OCF_2CF_2OCF_2$— is preferred.

<Group A-O-Q->

The following groups may be mentioned as specific examples of group A-O-Q- when group Q is a single bond.

$CF_3-O-$, $CF_3CF_2-O-$, $CF_3CF_2CF_2-O-$.

The following groups may be mentioned as specific examples of group A-O-Q- when group Q is $-Q^1-O-CH_2-$.

$CF_3-O-CHFCF_2-O-CH_2-$, $CF_3CF_2-O-CHFCF_2-O-CH_2-$, $CF_3CF_2CF_2-O-CHFCF_2-O-CH_2-$, $CF_3CF_2CF_2CF_2O-CHFCF_2-O-CH_2-$, $CF_3CF_2CF_2CF_2CF_2-O-CHFCF_2-O-CH_2-$, $CF_3-O-CF_2CF_2-O-CHFCF_2-O-CH_2-$, $CF_3CF_2-O-CF_2CF_2-O-CHFCF_2-O-CH_2-$, $CF_3-O-CF_2CF_2OCF_2CF_2-O-CHFCF_2-O-CH_2-$, $CF_3CF_2-O-CF_2CF_2OCF_2CF_2-O-CHFCF_2-O-CH_2-$, $CF_3CF_2CF_2-O-CF(CF_3)CF_2-O-CHFCF_2-O-CH_2-$, $CF_3CF_2CF_2-O-CF(CF_3)CF_2OCF(CF_3)CF_2-O-CHFCF_2-O-CH_2-$.

The following groups may be mentioned as specific examples of group A-O-Q- when group Q is $-Q^1-CH_2-$.

$CF_3-O-CF_2-CH_2-$, $CF_3CF_2-O-CF_2-CH_2-$, $CF_3-O-CF_2CF_2OCF_2-CH_2-$, $CF_3CF_2-O-CF_2CF_2OCF_2-CH_2-$, $CF_3-O-CF_2CF_2OCF_2CF_2OCF_2-CH_2-$, $CF_3CF_2-O-CF_2CF_2OCF_2CF_2OCF_2-CH_2-$.

The following groups may be mentioned as specific examples of group A-O-Q- when group Q is $-CH_2-$.

$CF_3-O-CH_2-$, $CF_3CF_2-O-CH_2-$.

<$(C_bF_{2b}O)_d$>

In $(C_bF_{2b}O)_d$, b is an integer of from 1 to 10, and d is an integer of from 1 to 200, provided that when d is at least 2, $(C_bF_{2b}O)_d$ may be composed of at least two types of $C_bF_{2b}O$ different in b.

b is preferably an integer of from 1 to 4 with a view to sufficiently imparting abrasion resistance and fingerprint stain removability to the surface-treated layer to be formed by using compound (5-11a), and b is preferably 1 or 2 with a view to sufficiently imparting lubricity to the surface-treated layer. Therefore, with a view to sufficiently imparting abrasion resistance, fingerprint stain removability and lubricity to the surface-treated layer, $(C_bF_{2b}O)_d$ wherein b is an integer of from 1 to 4, and $(C_bF_{2b}O)_d$ wherein b is 1 or 2, may be combined in such a combination that b is different.

In a case where b is at least 2, $C_bF_{2b}$ may be linear or branched. With a view to sufficiently imparting fingerprint stain removability and lubricity to the surface-treated layer, linear is preferred.

d is preferably an integer of at least 2, more preferably an integer of at least 10, particularly preferably an integer of at least 20, with a view to sufficiently imparting water/oil repellency to the surface-treated layer to be formed by using compound (5-11a). If the number average molecular weight of compound (5-11a) is too large, the number of $-SiL_mR_n$ groups present per unit molecular weight is decreased, and abrasion resistance of the surface-treated layer to be formed by using compound (5-11a) will be lowered, and from such a viewpoint, d is preferably an integer of at most 150, more preferably an integer of at most 100, particularly preferably an integer of at most 80.

When d is at least 2, $(C_bF_{2b}O)_d$ may be one composed of at least two types of $C_bF_{2b}O$ different in b.

In $(C_bF_{2b}O)_d$, when at least two types of $C_bF_{2b}O$ different in b are present, the binding order of respective $C_bF_{2b}O$ is not limited. For example, in a case where $CF_2O$ and $CF_2CF_2O$ are present, $CF_2O$ and $CF_2CF_2O$ may be randomly arranged, or $CF_2O$ and $CF_2CF_2O$ may be alternately arranged. Otherwise, a block composed of a plurality of $CF_2O$ and a block composed of a plurality of $CF_2CF_2O$ may be linked.

$(C_bF_{2b}O)$ may, for example, be $(CF_2O)$, $(C_2F_4O)$, $(C_3F_6O)$, $(C_4F_8O)$, $(C_5F_{10}O)$ or the like. The combination of at least two types of $(C_bF_{2b}O)$ different in b may be any combination of at least two types among them. With a view to sufficiently imparting water/oil repellency, abrasion resistance, fingerprint stain removability to the surface-treated layer to be formed by using compound (5-11a), groups represented by the following formulae (8-1) to (8-6) are preferred, and a group represented by the following formula (8-1), a group represented by the following formula (8-2), a group represented by the following formula (8-3) or a group represented by the following formula (8-5) is particularly preferred.

$(CF_2CF_2O)_d$     (8-1)

$\{(CF_2CF_2O)_{d1}(CF_2CF_2CF_2CF_2O)_{d2}\}$     (8-2)

$\{(CF_2O)_{d1}(CF_2CF_2O)_{d2}\}$     (8-3)

$(CF(CF_3)CF_2O)_d$     (8-4)

$(CF_2CF_2CF_2O)_d$     (8-5)

$\{(CF_2O)_{d1}(CF(CF_3)CF_2O)_{d2}\}$     (8-6)

Each of d1 and d2 is an integer of at least 1, provided that d1+d2 is an integer of from 2 to 200. Further, in group (8-2), the binding order of d1 number of $(CF_2CF_2O)$ and d2 number of $(CF_2CF_2CF_2CF_2O)$ is not limited. The same applies to group (8-3) and group (8-6).

Among them, $\{(CF_2O)_{d1}(CF_2CF_2O)_{d2}\}$ is preferably $CF_2O\{(CF_2O)_{d1-1}(CF_2CF_2O)_{d2}\}$ (wherein the left hand side $CF_2O$ is bonded to Q in the formula (1)) from the viewpoint of production efficiency of compound (3A1).

With a view to sufficiently imparting water/oil repellency, abrasion resistance and fingerprint stain removability to the surface-treated layer to be formed by using compound (5-11a), d1 is preferably an integer of at least 2, more preferably an integer of at least 5, particularly preferably an integer of at least 10. If the number average molecular weight of compound (5-11a) is too large, the number of -SiL$_m$R$_n$ groups present per unit molecular weight is decreased, and abrasion resistance of the surface-treated layer to be formed by using compound (5-11a) is lowered, and from such a viewpoint, d1 is preferably an integer of at most 100, more preferably an integer of at most 80, particularly preferably an integer of at most 50.

With a view to sufficiently imparting water/oil repellency, abrasion resistance and fingerprint stain removability to the surface-treated layer, d2 is preferably an integer of at least 2, more preferably an integer of at least 5, particularly preferably an integer of at least 10. If the number average molecular weight of compound (5-11a) is too large, the number of -SiL$_m$R$_n$ groups present per unit molecular weight is decreased, and abrasion resistance of the surface-treated layer to be formed by using compound (5-11a) is lowered, and from such a viewpoint, d2 is preferably an integer of at most 100, more preferably an integer of at most 80, particularly preferably an integer of at most 50.

Compound (3A1) can be produced as a mixture of plural types of compounds different in the number of d in (C$_b$F$_{2b}$O)$_d$. In such a case, the average value of d as the mixture is preferably from 1 to 200, particularly preferably from 2 to 150. Further, compound (3A1) can be produced as a mixture of plural types of compounds different in the numbers of d1 and d2. In such a case, the average value of d1 as the mixture is preferably from 1 to 100, and the average value of d2 is preferably from 1 to 100.

<Group X>

X is a divalent organic group having no CF$_2$O. X may, for example, be preferably a C$_{1-6}$ fluoroalkylene group or a C$_{1-6}$ alkylene group. From the viewpoint of production efficiency, a C$_{1-6}$ fluoroalkylene group having at least one hydrogen atom, is preferred, and a group represented by the following formula (6) is particularly preferred.

$$-(CF_2)_a CFX^1-CH_2 \tag{6}$$

Here, in the formula (6), a is from 0 to 2, and X$^1$ is F or CF$_3$.

Group (6) may, for example, be —CF$_2$CH$_2$—, —CF$_2$CF$_2$CH$_2$—, —CF$_2$CF$_2$CF$_2$CH$_2$— or —CF(CF$_3$)CH$_2$—.

Group (3) of compound (3A1) may be introduced by a method wherein a raw material compound having a 3-halopropyl group at a terminal of its molecule is subjected to dehydrohalogenation to convert the terminal of the molecule to a 2-propenyl group; or a method wherein a compound having a hydroxy group at a terminal of its molecule is reacted with an allyl halide to introduce an allyloxy group (—O—CH$_2$CH═CH$_2$) at the terminal of the molecule. As compound (3A1), a commercial product may also be used.

Preferred Embodiment of Compound (3A)

As compound (3A), compounds of the following formulae are preferred.

$$CH_3-R^{41}-O-CH_2CH=CH_2,$$

$$CH_3-R^{41}-O-(C_yH_{2y}O)_{y1}-CH_2CH=CH_2,$$

$$CH_3-R^{41}-CH_2CH=CH_2.$$

$$\underset{O}{\underset{\diagdown\diagup}{CH_2CH}}-R^{41}-O-CH_2CH=CH_2$$

Among compounds (3A), as compound (3A1), compounds of the following formulae are preferred.

When Q is a single bond, the following compounds (311) to (313) may be mentioned.

$$A-O-(C_bF_{2b}O)_d-CF_2CH_2-O-CH_2CH=CH_2 \tag{311}$$

$$A-O-(C_bF_{2b}O)_d-CF_2CF_2CH_2-O-CH_2CH=CH_2 \tag{312}$$

$$A-O-(C_bF_{2b}O)_d-CF_2CF_2CF_2CH_2-O-CH_2CH=CH_2 \tag{313}$$

When Q is -Q$^1$-O—CH$_2$—, the following compounds (321) and (322) and compounds (331) to (338) may be mentioned.

$$A-O-CHFCF_2-O-CH_2-(C_bF_{2b}O)_d-CF_2CH_2-O-CH_2CH=CH_2 \tag{321}$$

$$A-O-CHFCF_2-O-CH_2-(C_bF_{2b}O)_d-CF_2CF_2CF_2CH_2-O-CH_2CH=CH_2 \tag{322}$$

$$A-O-CF_2CF_2-O-CHFCF_2-O-CH_2-(C_bF_{2b}O)_d-CF_2CH_2-O-CH_2CH=CH_2 \tag{331}$$

$$A-O-CF_2CF_2-O-CHFCF_2-O-CH_2-(C_bF_{2b}O)_d-CF_2CF_2CF_2CH_2-O-CH_2CH=CH_2 \tag{332}$$

$$A-O-CF_2CF_2OCF_2CF_2-O-CHFCF_2-O-CH_2-(C_bF_{2b}O)_d-CF_2CH_2-O-CH_2CH=CH_2 \tag{333}$$

$$A-O-CF_2CF_2OCF_2CF_2-O-CHFCF_2-O-CH_2-(C_bF_{2b}O)_d-CF_2CF_2CF_2CH_2-O-CH_2CH=CH_2 \tag{334}$$

$$A-O-CF(CF_3)CF_2-O-CHFCF_2-O-CH_2-(C_bF_{2b}O)_d-CF_2CH_2-O-CH_2CH=CH_2 \tag{335}$$

$$A-O-CF(CF_3)CF_2-O-CHFCF_2-O-CH_2-(C_bF_{2b}O)_d-CF_2CF_2CF_2CH_2-O-CH_2CH=CH_2 \tag{336}$$

$$A-O-CF(CF_3)CF_2OCF(CF_3)CF_2-O-CHFCF_2-O-CH_2-(C_bF_{2b}O)_d-CF_2CH_2-O-CH_2CH=CH_2 \tag{337}$$

$$A-O-CF(CF_3)CF_2OCF(CF_3)CF_2-O-CHFCF_2-O-CH_2-(C_bF_{2b}O)_d-CF_2CF_2CF_2CH_2-O-CH_2CH=CH_2 \tag{338}$$

When Q is -Q$^1$-CH$_2$—, the following compounds (343) to (348) may be mentioned.

$$A-O-CF_2-CH_2-(C_bF_{2b}O)_d-CF_2CH_2-O-CH_2CH=CH_2 \tag{343}$$

$$A-O-CF_2-CH_2-(C_bF_{2b}O)_d-CF_2CF_2CF_2CH_2-O-CH_2CH=CH_2^1 \tag{344}$$

$$A-O-CF_2CF_2OCF_2-CH_2-(C_bF_{2b}O)_d-CF_2CH_2-O-CH_2CH=CH_2 \tag{345}$$

$$A-O-CF_2CF_2OCF_2-CH_2-(C_bF_{2b}O)_d-CF_2CF_2CF_2CH_2-O-CH_2CH=CH_2 \tag{346}$$

$$A-O-CF_2CF_2OCF_2CF_2OCF_2-CH_2-(C_bF_{2b}O)_d-CF_2CH_2-O-CH_2CH=CH_2 \tag{347}$$

$$A-O-CF_2CF_2OCF_2CF_2OCF_2-CH_2-(C_bF_{2b}O)_d-CF_2CF_2CF_2CH_2-O-CH_2CH=CH_2 \tag{348}$$

When Q is —CH$_2$, the following compounds (341) and (342) may be mentioned.

$$A-O-CH_2-(C_bF_{2b}O)_d-CF_2CH_2-O-CH_2CH=CH_2 \tag{341}$$

$$A-O-CH_2-(C_bF_{2b}O)_d-CF_2CF_2CF_2CH_2-O-CH_2CH=CH_2 \tag{342}$$

(Compound (3B))

Compound (3B) is represented by the following formula (3B) and has two groups (3). Therefore, by a reaction of compound (3B) and compound (4), usually, a compound having two groups (5) and a compound having one group (5) will be formed. For example, in the case of using compound (41) as compound (4), a compound represented by the following formula (5-121) with two groups (5-1), and a compound represented by the following formula (5-122) with one group (5-1) will be formed. Compound (5-121) is a compound in which both of the two groups (3) in compound (3B) are hydrosilylated, and compound (5-122) is a compound wherein one of the two groups (3) in compound (3B) is hydrosilylated. Thus, in a case where compound (3) having a plurality of groups (3) is used, usually a compound wherein all of the plurality of groups (3) are hydrosilylated and a compound wherein only some of them are hydrosilylated, will be formed.

  (3B)

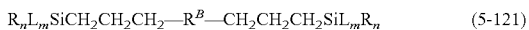  (5-121)

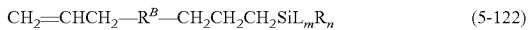  (5-122)

$R^B$ in the formula (3B) is a single bond, or a divalent group capable of bonding to two $-CH_2CH=CH_2$. The divalent group may, for example, be a divalent organic group, $-O-$ or $-S-$.

The divalent organic group may, for example, be an alkylene group, an alkenylene group, an alkynylene group, an arylene group, an aralkylene group or a divalent organic group having a heterocyclic ring. The alkylene, alkenylene and alkynylene groups may have, between carbon-carbon atoms, or at their one or both terminals, at least one divalent group selected from the group consisting of $-O-$, $-S-$, $-CO-O-$, $-CO-S-$, $-CO-NH-$, $-NH-CO-O-$, $-O-CO-$, $-S-CO-$, $-NH-CO-$ and $-O-CO-NH-$. Further, the divalent organic group may be a halogenated organic group having some or all of hydrogen atoms bonded to the carbon atoms substituted by halogen atoms.

When $R^B$ is a divalent organic group, as mentioned above, it is preferred that both bonding terminals are etheric oxygen atoms. Further, $R^B$ preferably has a polyoxyalkylene chain or a polyoxyfluoroalkylene chain. The polyoxyfluoroalkylene chain may be a polyoxyperfluoroalkylene chain.

Compound (3) having a polyoxyalkylene chain or a polyoxyfluoroalkylene chain tends to be a relatively high molecular weight compound in many cases, and as will be described below, the present invention is suitable as a method for producing compound (5) from such a relatively high molecular weight compound (3).

RB is preferably a single bond, $-O-$, $-O-R^{B1}-O-$, $-O-(C_yH_{2y}O)_{y1}-$, $-O-R^{B1}-O-(C_yH_{2y}O)_{y1}-$, $R^{B1}$, $-R^{B1}-O-$, $-O-R^{B1}-O-(C_yH_{2y}O)_{y1}-$ or the like.

$R^{B1}$ has the same meaning as $R^{A1}$ (except a single bond), and the same applies to the preferred embodiments. y and y1 are as described above, and preferred embodiments are also as described above.

As $R^B$, a group represented by the following formula (10) is also preferred.

  (10)

The symbols in the formula (10) have the same meanings as the symbols in the formula (1). Preferred embodiments are also the same. As a specific example of group $-O-Q-$, $-O-CH_2-$ may be mentioned where Q is $-CH_2-$.

A reaction mixture (hereinafter referred to also as "mixture (5-12a)") obtained by reacting compound (3B) wherein $R^B$ is group (10) (hereinafter referred to also as "compound (3B1)"), and compound (41), may be suitably used, for example, as a surface treatment agent to form a surface-treated layer having a water/oil repellency, on the surface of a substrate, such as a member constituting a surface of e.g. a touch panel to be touched by a finger. The mixture (5-12a) usually comprises a compound having both of two groups (3) in compound (3B1) hydrosilylated and a compound having one of them hydrosilylated.

Further, compound (3B1) may be a mixture of at least two compounds different in at least one of Q, $(C_bF_{2b}O)_d$ and X.

Two groups (3) in compound (3B1) may be introduced by, for example, a method wherein a compound having 3-halopropyl groups at both terminals of its molecule is subjected to dehydrohalogenation to convert both terminals of the molecule to 2-propenyl groups; or a method wherein a compound having hydroxy groups at both terminals of its molecule, is reacted with an allyl halide, to introduce allyloxy groups ($-O-CH_2CH=CH_2$) at both terminals of the molecule. As compound (3B1), a commercial product may also be used.

Preferred Embodiment of Compound (3B)

As compound (3B), compounds of the following formulae are preferred.

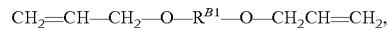

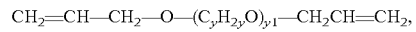

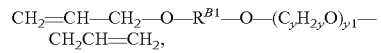

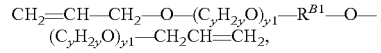

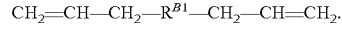

Among compounds (3B), as compound (3B1), the following compounds (3410) to (3430) wherein Q is $-CH_2-$ may be mentioned.

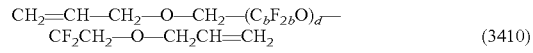  (3410)

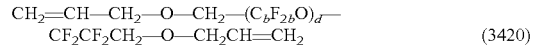  (3420)

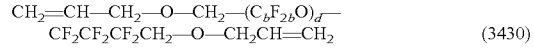  (3430)

(Compound (3C))

Compound (3C) is represented by the above formula (3C) and has three groups (3). Therefore, by a reaction of compound (3C) and compound (4), usually, a compound having three groups (5), a compound having two groups (5) and a compound having one group (5) will be formed.

As compound (3C), for example, a compound represented by the following formula (3C1) to be derived from a trifunctional alcohol, may be mentioned.

  (3C1)

In the formula, $R^c$ is a trivalent group, β is an integer of from 1 to 10, and γ is an integer of from 0 to 500. As the trivalent group, a trivalent organic group may be mentioned.

Further, as a compound having at least four groups (3), for example, a compound represented by the following formula (3D1) to be derived from a polyfunctional alcohol, may be mentioned.

  (3D1)

In the formula, $R^D$ is a tetravalent or higher valent group, and β and γ are as defined above. δ is an integer of at least 4, and the same integer as the valence of $R^D$. As the tetravalent or higher group, a tetravalent or higher valent organic group may be mentioned.

(Number Average Molecular Weight of Compound (3))

The number average molecular weight of compound (3) is not limited, and it may be selected depending on e.g. the application of compound (5). In the case of producing compound (5-11a) or mixture (5-12a) suitable for a surface treatment agent, the number average molecular weights of compound (3A1) and compound (3B1) are preferably from 500 to 10,000, particularly preferably from 1,000 to 8,000.

Further, according to the production method of the present invention, it is possible to produce compound (5) with high selectivity, whereby a reaction mixture obtained by the reaction with compound (4) may be used as it is, without purification by distillation or the like, in an application as a surface treatment agent. Thus, the production method of the present invention is particularly effective in a case where a compound having a high molecular weight with a number average molecular weight of from 200 to 20,000 is used as compound (3), and a reaction mixture thereby obtainable is also of a high molecular weight whereby purification by distillation itself is difficult.

The number average molecular weight (Mn) of compound (3) is a value obtainable by the following method by means of NMR spectroscopy. For example, in the case of compound (3A1) having group (1) or compound (3B1) having group (10), by $^{19}$F-NMR (solvent: CDCl$_3$, internal standard: CFCl$_3$), repeating units of $(C_bF_{2b}O)_d$ are identified, and at the same time, the number of repeating units is calculated, to calculate an average value of molecular weight of $(C_bF_{2b}O)_d$ per molecule. Then, by means of $^1$H-NMR (solvent: CDCl$_3$, internal standard: TMS), identification and quantification of terminal groups A and CH$_2$=CH—CH$_2$— are conducted, and based on the numbers of moles of the terminal groups, the number average molecular weight (Mn) of the compound is calculated.

With respect to compound (3) other than compound (3A1) and compound (3B1), by means of $^1$H-NMR, the structure of $R^A$, $R^B$, $R^C$ or $R^D$ is identified, and at the same time, identification and quantification of CH$_2$=CH—CH$_2$— as a terminal group are conducted, whereupon based on the numbers of moles of the terminal groups, the number average molecular weight (Mn) of the compound is calculated.

[Compound (4)]

Compound (4) is a silicon compound having an H—Si bond. Compound (4) may have one H—Si bond or a plurality of H—Si bonds in one molecule. Such a compound may be a silicon compound having an H—Si bond, such as a monosilane compound, a linear or cyclic polysilane compound, or a linear or cyclic polysiloxane compound, having a hydrogen atom bonded to some or all of Si atoms therein. As the polysilane compound or polysiloxane compound having an H—Si bond, preferred is an organopolysilane compound or organopolysiloxane compound having an organic group bonded to a silicon atom.

As compound (4), a hydrosilane compound represented by the following formula (41), a cyclic organohydropolysiloxane compound represented by the following formula (42), and a linear organohydropolysiloxane compound represented by the formula (43) are preferred.

$$HSiL_mR_n \quad (41)$$

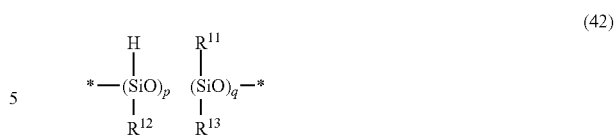
(42)

In the formula (42), * and * are linked to form a ring.

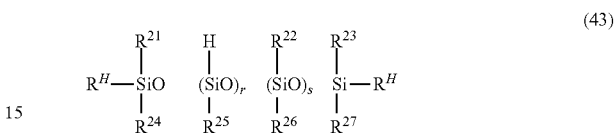
(43)

The symbols in the formulae (41), (42) and (43) represent the following. The symbols in the formulae represent the following:

L: a hydrolyzable group,
R: a monovalent hydrocarbon group,
$R^{11}$ to $R^{13}$ and $R^{21}$ to $R^{27}$: each independently a monovalent hydrocarbon group,
$R^H$: a hydrogen atom or a monovalent hydrocarbon group,
m and n: m is an integer of from 1 to 3, and n is an integer of from 0 to 2, provided m+n=3,
p and q: p is an integer of from 1 to 10, and q is an integer of from 0 to 9, provided p+q is an integer of from 3 to 10,
r and s: r is an integer of from 1 to 100, and s is an integer of from 0 to 1,000, provided r+s is an integer of from 1 to 1,000.

One type of compound (4) may be used alone, or two or more types thereof may be used in combination.

(Compound (41))

L may, for example, be an alkoxy group, a halogen atom, an acyl group or an isocyanate group. The alkoxy group is preferably a $C_{1-4}$ alkoxy group.

From the viewpoint of industrial production efficiency, L is preferably a $C_{1-4}$ alkoxy group or a halogen atom. The halogen atom may be a halogen atom as exemplified for $R^A$, and a chlorine atom is particularly preferred.

From the viewpoint of less outgassing during coating, and excellent storage stability of compound (5-1) to be produced, L is preferably a $C_{1-4}$ alkoxy group. When the alkoxy group is an ethoxy group, long-term storage stability of compound (5-1) will be excellent. When the alkoxy group is a methoxy group, at the time of using compound (5-1) as a surface treatment agent, the reaction time after application to a substrate will be shortened.

m is preferably 2 or 3, particularly preferably 3. It is considered that by the presence of a plurality of L in one molecule, the bond between silanol groups formed by hydrolysis of L and the substrate surface will be more strengthened, and at the same time, compounds (1) adjacent on the substrate surface are likely to be bonded to each other, to form a stronger surface-treated layer.

When m is at least 2, the plurality of L present in one molecule may be the same or different from one another. They are preferably the same from the viewpoint of availability of the raw material and simplicity of production.

R may, for example, be a monovalent saturated hydrocarbon group such as an alkyl group or a cycloalkyl group, a phenyl group, an alkenyl group or a 2-propenyl group. As a monovalent hydrocarbon group, a monovalent saturated hydrocarbon group or a phenyl group is particularly preferred. The number of carbon atoms in the monovalent saturated hydrocarbon group is preferably 1 to 6, more preferably from 1 to 3, particularly preferably 1 or 2.

R is, in view of simplicity of synthesis, preferably a $C_{1-6}$ alkyl group, more preferably a $C_{1-3}$ alkyl group, particularly preferably a 1-2 alkyl group.

n is an integer of from 0 to 2, provided m+n=3. n is preferably 0 or 1 (m is 3 or 2), particularly preferably n being 0 (m being 3). When n is 0 or 1 (m is 3 or 2), the bond between silanol groups formed by hydrolysis of L and the substrate surface, and the siloxane bond between silicon compounds adjacent on the substrate surface, tend to be readily formed.

-$SiL_mR_n$ may, for example, be —$Si(OCH_3)_3$, —$SiCH_3(OCH_3)_2$, —$Si(OCH_2CH_3)_3$, —$SiCl_3$, —$Si(OCOCH_3)_3$, or —$Si(NCO)_3$. From handling efficiency in industrial production, —$Si(OCH_3)_3$, —$SiCH_3(OCH_3)_2$, or —$Si(OCH_2CH_3)_3$ is preferred.

In the reaction of compound (41) with compound (3), compound (41) preferably has a molar ratio to group (3) of compound (3) being from 0.95 to 20, particularly preferably from 0.98 to 5. In the case of at least the lower limit value in the above range, compound (5-1) tends to be obtainable with higher selectivity. Further, the reaction rate of the hydrosilylation reaction will be excellent. In the case of at most the upper limit value in the above range, it is possible to obtain compound (5-1) with high selectivity while suppressing the amount of compound (41) to be used.

(Compound (42))

$R^{11}$ to $R^{13}$ are each independently a monovalent hydrocarbon group, for example, one indicated as R, and the same applies to the preferred embodiments. $R^{11}$ to $R^{13}$ may be the same hydrocarbon groups or different hydrocarbon groups, respectively, but they are preferably the same hydrocarbon groups.

p is preferably an integer of from 1 to 8, particularly preferably an integer of from 1 to 5. q is preferably an integer of from 0 to 7, particularly preferably an integer of from 0 to 4. p+q is preferably an integer of from 3 to 8, particularly preferably an integer of from 3 to 6. Within the above ranges, such a compound is easily available, and inter alia, a compound represented by the following formula (4-3) wherein p is 4 and q is 0, is preferred.

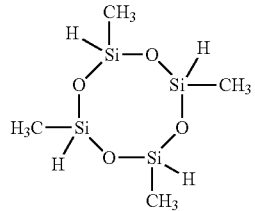
(4-3)

By a reaction of compound (42) with compound (3), a group represented by the following formula (5-2) will be formed.

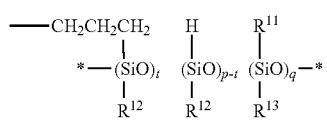
(5-2)

In the formula (5-2), the * and * are linked to form a ring. p, q and $R^{11}$ to $R^{13}$ are the same as described above. t is an integer of at most p (i.e. p−t is 0 or a positive integer).

In the reaction of compound (42) with compound (3), the molar ratio of H—Si bonds in compound (42), to groups (3) in compound (3) may optionally be adjusted depending on the purpose. For example, by adjusting the molar ratio to be at least 1, it is possible to permit H—Si bonds to remain, thereby to obtain a compound having a group represented by the above formula (5-2) (where p>t). Then, the remained (p−t) number of H—Si bonds, may be reacted with compound (a) having a —CH=$CH_2$ group other than compound (3). For example, in a case where a plurality of H—Si bonds are remained, to such H—Si bonds, compound (a) having a —CH=$CH_2$ group and a -$SiL_mR_n$ group may be reacted for hydrosilylation, whereby it is possible to produce a compound having a plurality of -$SiL_mR_n$ groups. Such compound (a) may, for example, be $CH_2$=$CHSi(OCH_3)_3$, $CH_2$=$CHSi(CH_3)(OCH_3)_2$, $CH_2$=$CHSi(OCH_2CH_3)_3$, $CH_2$=$CHSiCl_3$, or $CH_2$=$CHCH_2Si(OCH_3)_3$.

(Compound (43))

$R^{21}$ to $R^{27}$ are each independently a monovalent hydrocarbon group, for example, one indicated as R, and the same applies to the preferred embodiments. $R^{21}$ to $R^{27}$ may be the same hydrocarbon groups or different hydrocarbon groups, respectively, but they are preferably the same hydrocarbon groups.

$R^H$ is a hydrogen atom or a monovalent hydrocarbon group, and the monovalent hydrocarbon group may, for example, be one indicated as R, and the same applies to the preferred embodiments.

r is preferably an integer of from 1 to 50, particularly preferably an integer of from 1 to 20. s is preferably an integer of from 0 to 500, particularly preferably an integer of 0 to 200. r+s is preferably an integer of from 1 to 500, particularly preferably an integer of from 1 to 200. Within the above ranges, the raw material is readily available, and the production is simple.

By a reaction of compound (43) with compound (3), for example, in a case where RH is not a hydrogen atom, a group represented by the following formula (5-3) will be formed.

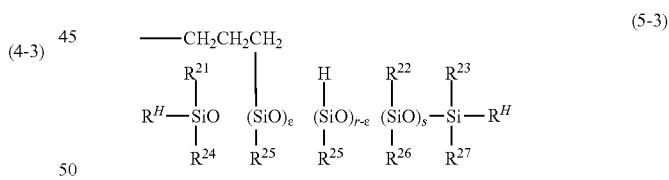
(5-3)

r, s and $R^{21}$ to $R^{27}$ are as defined above. ε is an integer of at most r (i.e. r−ε is 0 or a positive integer).

In the reaction of compound (43) with compound (3), the molar ratio of H—Si bonds in compound (43) to groups (3) in compound (3) may optionally be adjusted depending on the purpose. For example, by adjusting the molar ratio to be at least 1, it is possible to permit H—Si bonds to remain, thereby to obtain a compound having a group represented by the above formula (5-3) (where r>ε). And, it is also possible to let the remained (r−ε) number of H—Si bonds be reacted with the above-mentioned compound (a) having a —CH=$CH_2$ group other than compound (3). For example, in a case where a plurality of H—Si bonds are remained, to such H—Si bonds, the compound (a) may be reacted for hydrosilylation, whereby it is possible to produce a compound having a plurality of -$SiL_mR_n$ groups.

Further, in a case where $R^H$ in compound (43) is a hydrogen atom, compound (3) may sometimes react to at least one of the two Si—$R^H$ bonds in compound (43).

[Transition Metal Catalyst (C)]

As the transition metal catalyst (C), Groups 8 to 10 transition metal catalysts are preferred, and among them, a platinum (Pt) catalyst, a ruthenium (Ru) catalyst, or a rhodium (Rh) catalyst is preferred. A platinum catalyst is particularly preferred, since by combination with the after-described compound (D), compound (5) can readily be obtained with higher selectivity. Here, Groups 8 to 10 are group numbers by IUPAC Inorganic Chemical Nomenclature Revised Edition (1989).

The platinum catalyst may, for example, be a Pt/divinyltetramethyldisiloxane complex, a Pt/tetramethyltetravinylcyclotetrasiloxane complex, chloroplatinic acid or platinum oxide. Among them, either one of a Pt/divinyltetramethyldisiloxane complex and a Pt/tetramethyltetravinylcyclotetrasiloxane complex is particularly preferred, since by combination with the after-described compound (D), compound (5) can readily be obtained with higher selectivity.

As the amount of the transition metal catalyst (C) to be used, the mass ratio to compound (3) is preferably from 0.01 to 1,000 ppm, particularly preferably from 1 to 100 ppm. Within the above range, the reaction proceeds under proper reaction conditions, and there will be less coloration due to the catalyst.

(Compound (D))

Compound (D) has a group represented by the following formula (D).

—S(=O)— (D)

Compound (D) is a sulfoxide compound such as tetramethylene sulfoxide (hereinafter referred to also as "TMSO") or dim ethyl sulfoxide (hereinafter referred to also as "DMSO").

One type of compound (D) may be used alone, or two or more types thereof may be used in combination.

By using such compound (D) in combination with the transition metal catalyst (C), compound (5) can be obtained with high selectivity.

Compound (D) has a large donor number. The donor number is one of solvent parameters and an index for electron (pair) donating ability. The larger the donor number of the compound, the larger the electron (pair) donating ability, and the higher the coordination ability. When compound (D) having a large donor number is used in combination with the transition metal catalyst (C), such compound (D) is coordinated with a transition metal in the transition metal catalyst (C), whereby coordination of compound (3) with the transition metal is considered to be controlled. As a result, it is considered possible to readily obtain the desired compound (5) selectively.

The donor number is the amount of heat when a compound and $SbCl_5$ form a 1:1 adduct, and the donor numbers of various compounds, a calculation method for the donor number, etc. are disclosed, for example, in the following reference literatures (1) and (2). (1) Pure & Appl. Chem., Vol. 41, No. 3, pp. 291-326, 1975. (2) Pure & Appl. Chem., Vol. 58, No. 8, pp. 1153-1161, 1986.

The amount of compound (D) to be used, is preferably from 0.001 to 1,000 parts by mass, particularly preferably from 0.01 to 10 parts by mass, to 100 parts by mass of compound (3). Within the above range, compound (5) can be readily obtained with higher selectivity.

The mass ratio in amount of compound (D) to transition metal catalyst (C) to be used (i.e. compound (D):transition metal catalyst (C)) is preferably from 10:1 to 10,000:1, particularly preferably from 20:1 to 1,000:1. Within the above range, compound (5) can be readily obtained with higher selectivity.

[Hydrosilylation Reaction]

The hydrosilylation reaction of compound (3) and compound (4) in the presence of transition metal catalyst (C) and compound (D), is carried out by using, for example, a container made of a resin such as a polyolefin or a fluororesin, a glass container, a container made of metal such as SUS, or a lined container coated with a fluorinated resin.

The reaction temperature is preferably from 0 to 100° C., particularly preferably from 20 to 50° C., whereby the reaction proceeds sufficiently and formation of by-products is suppressed. The reaction time is preferably from 1 to 100 hours, particularly preferably from 2 to 20 hours. The reaction pressure is preferably from −0.01 to 1 MPaG, more preferably from 0 to 0.1 MPaG. "G" in "MPaG" represents the gauge pressure.

(Solvent)

The hydrosilylation reaction may be carried out in the presence or absence of a solvent. In a case where it is conducted in the presence of a solvent, as the solvent, an organic solvent is preferred. The organic solvent may be a fluorinated organic solvent or a non-fluorinated organic solvent, or both solvents may be used.

The fluorinated organic solvent may, for example, be a fluorinated alkane, a fluorinated aromatic compound, a fluoroalkyl ether, a fluorinated alkylamine or a fluoroalcohol.

As the fluorinated alkane, a compound having from 4 to 8 carbon atoms is preferred. Commercial products may, for example, be $C_6F_{13}H$ (AC-2000: trade name, manufactured by Asahi Glass Company, Limited), $C_6F_{13}C_2H_5$ (AC-6000: trade name, manufactured by Asahi Glass Company, Limited), $C_2F_5CHFCHFCF_3$ (Vertrel: trade name, manufactured by DuPont), etc.

The fluorinated aromatic compound may, for example, be hexafluorobenzene, trifluoromethylbenzene, perfluorotoluene, 1,3-bis(trifluoromethyl)benzene or 1,4-bis (trifluoromethyl)benzene.

As the fluoroalkyl ether, a compound having from 4 to 12 carbon atoms is preferred. Commercial products may, for example, be $CF_3CH_2OCF_2CF_2H$ (AE-3000: trade name, manufactured by Asahi Glass Company, Limited), $C_4F_9OCH_3$ (Novec-7100: trade name, manufactured by 3M), $C_4F_9OC_2H_5$ (Novec-7200: trade name, manufactured by 3M), $C_6F_{13}OCH_3$ (Novec-7300: trade name, manufactured by 3M), etc.

The fluorinated alkylamine may, for example, be perfluorotripropylamine or perfluorotributylamine.

The fluoroalcohol may, for example, be 2,2,3,3-tetrafluoropropanol, 2,2,2-trifluoroethanol or hexafluoroisopropanol.

As the fluorinated organic solvent, it is preferred to use at least one fluorinated organic solvent selected from the group consisting of fluorinated alkanes, fluorinated aromatic compounds and fluoroalkyl ethers, from the viewpoint of compatibility of compound (3) with other compounds.

As the non-fluorinated organic solvent, a compound composed solely of hydrogen atoms and carbon atoms, or a compound composed solely of hydrogen atoms, carbon atoms and oxygen atoms, is preferred, and a hydrocarbon-type organic solvent, a ketone-type organic solvent, an ether-type organic solvent, or an ester-type organic solvent, may be mentioned.

The hydrocarbon-type organic solvent may, for example, be preferably hexane, heptane or cyclohexane.

The ketone-type organic solvent may, for example, be preferably acetone, methyl ethyl ketone, or methyl isobutyl ketone.

The ether-type organic solvent may, for example, be preferably diethyl ether, tetrahydrofuran, or tetraethylene glycol dimethyl ether.

The ester-type organic solvent may, for example, be preferably ethyl acetate, or butyl acetate.

As the non-fluorinated organic solvent, a hydrocarbon-type organic solvent is particularly preferred from the viewpoint of compatibility of compound (3) with other compounds, etc.

As the amount of the solvent to be used, the mass ratio to 100 parts by mass of compound (3) is preferably from 0.1 to 10,000 parts by mass, particularly preferably from 1 to 1,000 parts by mass. Within the above range, there will be an effect to let respective compounds be compatibilized with one another, and the reaction conditions may be made mild.

Thus, according to the method for producing a silicon compound of the present invention, which comprises reacting compound (3) having a 2-propenyl group and silicon compound (4) having an Si—H bond in the presence of the transition metal catalyst (C) and the compound (D), it is possible to carry out the hydrosilylation reaction of compound (3) with high selectivity by a simple and easy method, thereby to obtain compound (5) with high selectivity. Further, it is possible to suppress formation of a by-product having a 1-propenyl group with the double bond moved to inside.

Therefore, in a case where compound (3) is a high molecular weight compound, and the separation of the desired compound and the by-product by e.g. distillation purification, is difficult, even when the reaction mixture is used as it is without purification, as a surface treatment agent, if necessary, as mixed with other components such as a solvent, etc., a sufficient function can be exhibited. Further, the odor problem due to formation of a by-product having a 1-propenyl group can also be suppressed.

EXAMPLES

Now, the present invention will be described in further detail with reference to Examples, but the present invention is not limited to these Examples.

Hereinafter, "%" is "mass %" unless otherwise specified. Ex. 2, 3, 16, 18, 20, 22, 24, 26, 28, 30, 32, 33, 35, 36, 38, 39, 41, 42, 44, 45, 47 and 48 are Examples of the present invention, and Ex. 1, 4 to 15, 17, 19, 21, 23, 25, 27, 29, 31, 34, 37, 40, 43 and 46 are Comparative Examples.

Hereinafter, fluorinated organic solvent $C_6F_{13}H$ will be referred to as "AC-2000" (trade name, manufactured by Asahi Glass Company, Limited), and fluorinated organic solvent $C_6F_{13}C_2H_5$ will be referred to as "AC-6000" (trade name, manufactured by Asahi Glass Company, Limited).

[Compound (3)]

As compound (3), the following compounds (3-1) to (3-4), compounds (3-6) to (3-12) and mixture (3-5) were used.

Production Example 1

Production of Compound (3-1)

The following compound (3-1a) was obtained by the method in Ex. 1 in WO2009/008380.

$$CF_3-O-(CF_2CF_2O)_d-CF_2CH_2OH \quad (3\text{-}1a)$$

NMR spectrum of compound (3-1a):
$^1$H-NMR (300.4 MHz, solvent: $CDCl_3$, standard: TMS) δ (ppm): 1.9 (1H), 3.9 (2H).
$^{19}$F-NMR (282.7 MHz, solvent: $CDCl_3$, standard: $CFCl_3$) δ (ppm): −56.2 (3F), −81.4 (2F), −89.5 (26F), −91.4 (2F).
The average value of the number of units d: 7.
The number average molecular weight: 1,000.

In a two-necked eggplant flask of 200 mL, 50.0 g of compound (3-1a), 2.1 g of tetrabutylammonium hydrogen sulfate, 18.0 g of allyl bromide and 26.4 g of a 30% aqueous sodium hydroxide solution were added and stirred at 60° C. for 8 hours. After completion of the reaction, 50 g of AC-2000 was added, followed by washing once with a dilute aqueous hydrochloric acid solution to recover the organic phase. The recovered organic phase was passed through a silica gel column, and the recovered solution was concentrated by an evaporator to obtain 50.2 g (yield: 96.5%) of compound (3-1).

$$CF_3-O-(CF_2CF_2O)_d-CF_2CH_2-O-CH_2-CH=CH_2 \quad (3\text{-}1)$$

NMR spectrum of compound (3-1):
$^1$H-NMR (300.4 MHz, solvent: $CDCl_3$, standard: TMS) δ (ppm): 3.8 (2H), 4.1 (2H), 5.2 to 5.3 (2H), 5.9 (1H).
$^{19}$F-NMR (282.7 MHz, solvent: $CDCl_3$, standard: $CFCl_3$) δ (ppm): −56.3 (3F), −78.3 (2F), −89.5 (26F), −91.5 (2F).
The average value of the number of units d: 7.
The number average molecular weight of compound (3-1): 1,000.

Production Example 2

Production of Compound (3-2)

The following compound (3-2) was obtained by the method in Ex. 7 in WO2013/121986.

$$CF_3-O-(CF_2CF_2OCF_2CF_2CF_2CF_2O)_{d1}-(CF_2CF_2O)_{d2}CF_2CF_2CF_2CH_2-O-CH_2-CH=CH_2 \quad (3\text{-}2)$$

NMR spectrum of compound (3-2a):
$^1$H-NMR (300.4 MHz, solvent: $CDCl_3$, standard: TMS) δ (ppm): 3.8 (2H), 4.1 (2H), 5.2 (2H), 5.9 (1H).
$^{19}$F-NMR (282.7 MHz, solvent: $CDCl_3$, standard: $CFCl_3$) δ (ppm): −56.2 (3F), −84.1 (54F), −89.3 (54F), −91.4 (2F), −120.5 (2F), −126.6 (52F), −128.6 (2F).
The average value of the number of units d1: 13.
The average value of the number of units d2: 1
The number average molecular weight of compound (3-2): 4,700.

Production Example 3

Production of Compound (3-3)

In a two-necked eggplant flask of 100 mL, 30.0 g of the following compound (3-3a) (FLUOROLINK D4000: trade name, manufactured by Solvay Solexis Co., Ltd.), 0.64 g of tetrabutylammonium hydrogen sulfate, 4.5 g of allyl bromide and 6.0 g of a 30% sodium hydroxide aqueous solution were added and stirred at 60° C. for 8 hours. After completion of the reaction, 30 g of AC-2000 was added, followed by washing once with a dilute aqueous hydrochloric acid solution to recover the organic phase. The recovered organic phase was passed through a silica gel column, and the recovered solution was concentrated by an evaporator to obtain 29.7 g (yield: 97.1%) of compound (3-3).

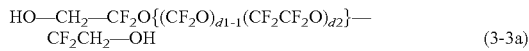
(3-3a)

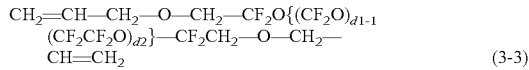
(3-3)

NMR spectrum of compound (3-3):

$^1$H-NMR (300.4 MHz, solvent: CDCl$_3$, standard: TMS) δ (ppm): 3.7 (4H), 4.1 (4H), 5.2 to 5.3 (4H), 5.9 (2H).

$^{19}$F-NMR (282.7 MHz, solvent: CDCl$_3$, standard: CFCl$_3$) δ (ppm): −52.3 to −55.7 (42F), −78.1 (2F), −80.2 (2F), −89.4 to −91.1 (84F).

The average value of the number of units (d1-1): 21.
The average value of the number of units d2: 21.
The number average molecular weight of compound (3-3): 4,100.

Production Example 4

Production of Compound (3-4)

In a three-necked flask of 300 mL, 2.9 g of a 20% KOH aqueous solution, 33 g of tert-butyl alcohol, 110 g of 1,3-bis(trifluoromethyl)benzene and 220 g of compound (3-3a) were put, and 14.6 g of CF$_3$CF$_2$CF$_2$—O—CF═CF$_2$ was added. Under a nitrogen atmosphere, the mixture was stirred at 40° C. for 20 hours. It was washed once with a dilute aqueous hydrochloric acid solution, and the organic phase was recovered and concentrated by an evaporator to obtain 233 g of a crude product (a). The crude product (a) was diluted with 115 g of AC-2000 and developed by silica gel column chromatography for fractionation. As the developing solvents, AC-2000, AC-2000/CF$_3$CH$_2$OCF$_2$CF$_2$H (AE-3000: trade name, manufactured by Asahi Glass Company, Limited) (mass ratio: 1/2), and AE-3000/acetone (mass ratio: 2/1) were sequentially used. With respect to each fraction, the structure of terminal groups and the average values of the numbers of units of constituting units (d1, d2) were obtained from the integral values of $^1$H-NMR and $^{19}$F-NMR. Thus, it was found that in the crude product (a), compound (3-4a), compound (3-4b) and compound (3-3a) were contained in amounts of 50 mol %, 25 mol % and 25 mol %, respectively. Here, 105.1 g (yield: 44.8%) of compound (3-4a) was obtained.

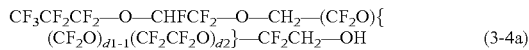
(3-4a)

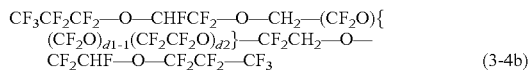
(3-4b)

NMR spectrum of compound (3-4a):

$^1$H-NMR (300.4 MHz, solvent: CDCl$_3$, standard: TMS) δ (ppm): 3.9 (2H), 4.2 (2H), 5.8 to 6.0 (1H).

$^{19}$F-NMR (282.7 MHz, solvent: CDCl$_3$, standard: CFCl$_3$) δ (ppm): −52.4 to −55.8 (42F), −78.8 (1F), −80.8 (1F), −81.4 (1F), −82.2 (3F), −83.5 (1F), −85.3 to −88.2 (2F), −89.4 to −91.1 (86F), −130.5 (2F), −145.1 (1F).

The average value of the number of units (d1-1): 21.
The average value of the number of units d2: 21.
The number average molecular weight of compound (3-4a): 4,300.

NMR spectrum of compound (3-4b):

$^1$H-NMR (300.4 MHz, solvent: CDCl$_3$, standard: TMS) δ (ppm): 4.2 (4H), 5.8 to 6.0 (2H).

$^{19}$F-NMR (282.7 MHz, solvent: CDCl$_3$, standard: CFCl$_3$) δ (ppm): −52.4 to −55.8 (42F), −78.8 (2F), −80.7 (2F), −82.2 (6F), −85.3 to −88.2 (4F), −89.4 to −91.1 (88F), −130.5 (4F), −145.1 (2F).

The average value of the number of units (d1-1): 21.
The average value of the number of units d2: 21.
The number average molecular weight of compound (3-4b): 4,500.

In a two-necked eggplant flask of 100 mL, 52.0 g of compound (3-4a), 0.52 g of tetrabutylammonium hydrogen sulfate, 4.4 g of allyl bromide and 6.5 g of a 30% sodium hydroxide aqueous solution were added and stirred at 60° C. for 8 hours. After completion of the reaction, 50 g of AC-2000 was added, followed by washing once with a dilute aqueous hydrochloric acid solution to recover the organic phase. The recovered organic phase was passed through a silica gel column, and the recovered solution was concentrated by an evaporator to obtain 52.4 g (yield: 99.9%) of compound (3-4).

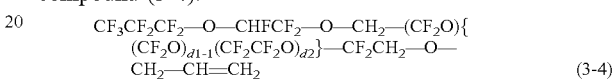
(3-4)

NMR spectrum of compound (3-4):

$^1$H-NMR (300.4 MHz, solvent: CDCl$_3$, standard: TMS) δ (ppm): 3.7 (2H), 4.1 (2H), 4.2 (2H), 5.2 to 5.3 (2H), 5.8 to 6.0 (2H).

$^{19}$F-NMR (282.7 MHz, solvent: CDCl$_3$, standard: CFCl$_3$) δ (ppm): −52.3 to −55.7 (42F), −78.1 (1F), −78.7 (1F), −80.2 (1F), −80.7 (1F), −82.2 (3F), −85.4 to −88.2 (2F), −89.4 to −91.1 (86F), −130.5 (2F), −145.1 (1F).

The average value of the number of units (d1-1): 21.
The average value of the number of units d2: 21.
The number average molecular weight of compound (3-4): 4,300.

Production Example 5

Synthesis of Mixture (3-5)

In a two-necked eggplant flask of 100 mL, 26.0 g of the crude product (a) obtained in Production Example 4, 0.26 g of tetrabutylammonium hydrogen sulfate, 2.2 g of allyl bromide and 3.3 g of a 30% sodium hydroxide aqueous solution were added and stirred at 60° C. for 8 hours. After completion of the reaction, 30 g of AC-2000 was added, followed by washing once with a dilute aqueous hydrochloric acid solution to recover the organic phase. The recovered organic phase was passed through a silica gel column, and the recovered solution was concentrated by an evaporator to obtain 26.1 g (yield: 99.0%) of mixture (3-5).

Mixture (3-5) is a mixture of compound (3-3), compound (3-4) and compound (3-4b) in a ratio of 25:50:25 (mol %).

Production Example 6

Synthesis of Compound (3-6)

In an eggplant flask of 100 mL, 30.0 g of compound (3-4a), 0.9 g of sodium fluoride powder and 30 g of dichloropentafluoropropane (AK-225: trade name, manufactured by Asahi Glass Company, Limited) were put, and 3.5 g of CF$_3$CF$_2$CF$_2$OCF(CF$_3$)COF was added. Under a nitrogen atmosphere, the mixture was stirred at 50° C. for 24 hours. After removing the sodium fluoride powder by a pressure filter, excess CF$_3$CF$_2$CF$_2$OCF(CF$_3$)COF and AK-225 were distilled off under reduced pressure. The obtained crude product was diluted with AC-2000 and passed through a silica gel column, and the recovered solution was concentrated by an evaporator to obtain 31.8 g (yield: 98.8%) of compound (3-6d).

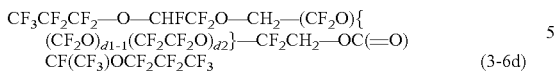
(3-6d)

NMR spectrum of compound (3-6d):
$^1$H-NMR (300.4 MHz, solvent: CDCl$_3$, standard: TMS) δ (ppm): 4.2 (2H), 4.7 (2H), 5.8 to 6.0 (1H).
$^{19}$F-NMR (282.7 MHz, solvent: CDCl$_3$, standard: CFCl$_3$) δ (ppm): −52.4 to −55.8 (42F), −78.8 to −88.2 (17F), −89.4 to −91.1 (86F), −130.3 (2F), −30.5 (2F), −132.5 (1F), −145.1 (1F).

The average value of the number of units (d1-1): 21.
The average value of the number of units d2: 21.
The number average molecular weight of compound (3-6d): 4,500.

An autoclave (made of nickel, inner volume: 1 L) was prepared, and at a gas outlet of the autoclave, a condenser kept at 20° C., a NaF pellet packed layer and a condenser kept at 0° C. were set in series. Further, a liquid returning line for returning a condensed liquid from the condenser kept at 0° C. to the autoclave, was installed.

Into the autoclave, 750 g of ClCF$_2$CFClCF$_2$OCF$_2$CF$_2$Cl (hereinafter referred to also as "CFE-419") was charged and stirred while maintaining the temperature at 25° C. Into the autoclave, nitrogen gas was blown at 25° C. for 1 hour, and then, 20% fluorine gas was blown at 25° C. for one hour at a flow rate of 2.0 L/hr. Then, while blowing 20% fluorine gas at the same flow rate, into the autoclave, a solution having 31.0 g of compound (3-6d) dissolved in 124 g of CFE-419, was injected over a period of 4.3 hours.

Then, while blowing 20% fluorine gas at the same flow rate, the internal pressure of the autoclave was pressurized up to 0.15 MPa (gauge pressure). Into the autoclave, 4 mL of a benzene solution containing 0.05 g/mL of benzene in CFE-419, was injected while heating from 25° C. to 40° C., and the benzene solution inlet of the autoclave was closed. After stirring for 15 minutes, 4 mL of the benzene solution was injected again while maintaining the temperature at 40° C., and the inlet was closed. The same operation was repeated three more times. The total amount of benzene injected was 0.17 g.

Further, while blowing 20% fluorine gas at the same flow rate, stirring was continued for 1 hour. Then, the pressure in the autoclave was returned to the atmospheric pressure, and nitrogen gas was blown for 1 hour. The content of the autoclave was concentrated by an evaporator to obtain 31.1 g (yield: 98.5%) of compound (3-6c).

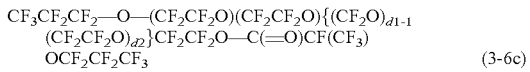
(3-6c)

NMR spectrum of compound (3-6c):
$^{19}$F-NMR (282.7 MHz, solvent: CDCl$_3$, standard: CFCl$_3$) δ (ppm): −52.4 to −55.7 (42F), −78.8 to −88.1 (11F), −89.4 to −91.1 (96F), −91.5 (2F), −130.3 (2F), −130.5 (2F), −132.5 (1F).

The average value of the number of units (d1-1): 21.
The average value of the number of units d2: 21.
The number average molecular weight of compound (3-6c): 4,600.

Into a round bottomed flask made of PFA, 30.0 g of compound (3-6c) and 60 g of AK-225 were charged. While stirring under cooling in an ice bath, under a nitrogen atmosphere, 2.0 g of methanol was slowly added dropwise from a dropping funnel. While bubbling with nitrogen, stirring was continued for 12 hours. The reaction mixture was concentrated by an evaporator to obtain 27.6 g (yield: 98.8%) of compound (3-6b).

(3-6b).

NMR spectrum of compound (3-6b):
$^1$H-NMR (300.4 MHz, solvent: CDCl$_3$, standard: TMS) δ (ppm): 3.9 (3H).
$^{19}$F-NMR (282.7 MHz, solvent: CDCl$_3$, standard: CFCl$_3$) δ (ppm): −52.4 to −55.8 (42F), −82.2 (3F), −89.4 to −91.1 (92F), −130.5 (2F).

The average value of the number of units (d1-1): 21.
The average value of the number of units d2: 21.
The number average molecular weight of compound (3-6b): 4,300.

In a three-necked eggplant flask of 100 mL, 0.18 g of lithium chloride was dissolved in 18.3 g of ethanol. To this, 25.0 g of compound (3-6b) was added, and while cooling in ice bath, a solution having 0.75 g of sodium borohydride dissolved in 22.5 g of ethanol was slowly dropwise added. Then, the ice bath was removed, and stirring was continued while slowly warming to room temperature. After stirring at room temperature for 12 hours, an aqueous solution of hydrochloric acid was dropwise added until the liquid became acidic. 20 mL of AC-2000 was added, followed by washing once with water and once with a saturated sodium chloride aqueous solution, to recover the organic phase. The recovered organic phase was concentrated by an evaporator to obtain 24.6 g (yield: 99.0%) of compound (3-6a).

(3-6a).

NMR spectrum of compound (3-6a):
$^1$H-NMR (300.4 MHz, solvent: CDCl$_3$, standard: TMS) δ (ppm): 3.9 (2H).
$^{19}$F-NMR (282.7 MHz, solvent: CDCl$_3$, standard: CFCl$_3$) δ (ppm): −52.4 to −55.7 (42F), −81.4 (1F), −82.2 (3F), −83.4 (1F), −89.4 to −91.1 (90F), −130.5 (2F).

The average value of the number of units (d1-1): 21.
The average value of the number of units d2: 21.
The number average molecular weight of compound (3-6a): 4,200.

In a two-necked eggplant flask of 100 mL, 20.0 g of compound (3-6a), 0.21 g of tetrabutylammonium hydrogen sulfate, 1.76 g of allyl bromide and 2.6 g of a 30% sodium hydroxide aqueous solution were added and stirred at 60° C. for 8 hours. After completion of the reaction, 20 g of AC-2000 was added, followed by washing once with a dilute aqueous hydrochloric acid solution to recover the organic phase. The recovered organic phase was passed through a silica gel column, and the recovered solution was concentrated by an evaporator to obtain 19.8 g (yield: 98.2%) of compound (3-6).

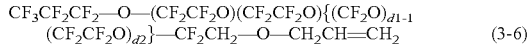
(3-6)

NMR spectrum of compound (3-6):
$^1$H-NMR (300.4 MHz, solvent: CDCl$_3$, standard: TMS) δ (ppm): 3.7 (2H), 4.1 (2H), 5.2 to 5.3 (2H), 5.9 (1H).
$^{19}$F-NMR (282.7 MHz, solvent: CDCl$_3$, standard: CFCl$_3$) δ (ppm): −52.3 to −55.7 (42F), −78.1 (1F), −80.1 (1F), −82.1 (3F), −89.4 to −91.1 (94F), −130.5 (2F).

The average value of the number of units (d1-1): 21.
The average value of the number of units d2: 21.
The number average molecular weight of compound (3-6): 4,300.

Compound (3-7): n-butyl allyl ether.
Compound (3-8): glycidyl allyl ether.
Compound (3-9): $CH_3O—(CH_2CH_2O)_{y1}—CH_2CH=CH_2$, the average value of the number of units y1: 10, the number average molecular weight: 510. (Uniox PKA-5009: trade name, manufactured by Nippon Oil & Fats Co., Ltd.).
Compound (3-10): $CH_2=CHCH_2O—(CH_2CH_2O)_{y1}—CH_2CH=CH_2$, the average value of the number of units y1: 10, the number average molecular weight: 540. (Uniox AA-480R: trade name, manufactured by Nippon Oil & Fats Co., Ltd.).
Compound (3-11): $CH_2=CHCH_2O—(C_3H_6O)_{y1}—CH_2CH=CH_2$, the average value of the number of units y1: 50, the number average molecular weight: 3,000. (UNI-SAFE PKA-5018: trade name, manufactured by Nippon Oil & Fats Co., Ltd.).
Compound (3-12): 1-octene.
[Compound (4)]
As compound (4), the following compounds were used.
Compound (4-1): $HSi(OCH_3)_3$.
Compound (4-2): $HSi(CH_3)(OCH_3)_2$.
Compound (4-3): compound represented by the above formula (4-3).
[Transition Metal Catalyst (C)]
As transition metal catalyst (C), the following compounds were used.
Compound (C1): Pt/divinyltetramethyldisiloxane complex (2.0% xylene solution).
Compound (C2): Pt/tetramethyltetravinylcyclotetrasiloxane complex (1.8% vinyl methyl cyclotetrasiloxane solution).
[Compound (D)]
As compound (D), the following compounds were used.
DMSO: dimethyl sulfoxide.
TMSO: tetramethylene sulfoxide.
[Compound (Dα)]
For comparison to compound (D), the following compounds (Dα) were used.
HMPA: hexamethylphosphoramide.
DMF: N,N-dimethylformamide.
Pyridine.
Tetramethylurea.
Acetone.
Toluene.
Hexane.
Methanol.
THF: tetrahydrofuran.
NMF: N-methyl formamide.
Triethylamine.
[Organic Solvent (E)]
As organic solvent (E), the following compounds were used.
Fluorinated organic solvent (E1): AC-2000.
Fluorinated organic solvent (E2): AC-6000.
Non-fluorinated organic solvent (E3): toluene.

Ex. 1 to 48

Into a sample bottle made of PP or a flask made of PFA, compound (3), compound (4), transition metal catalyst (C), compound (D) or compound (Dα) and organic solvent (E) in the charged amounts as shown in Tables 1 and 2 and a stirrer, were put, sealed and reacted under reaction conditions as shown in Tables 1 and 2. Here, in this specification, "room temperature" is from 20 to 30° C.

By $^1$H-NMR analysis of the reaction mixture after completion of the reaction, the conversion and selectivity of the reaction were calculated. The results are shown in Table 1 and Table 2.

Here, transition metal catalyst (C1) and transition metal catalyst (C2) were added in the form of a solution, as mentioned above. In the description of transition metal catalyst (C) in Table 1 and Table 2, "mg (solution)" means the mass as the solution, and "μg (catalyst)" means the net amount of transition metal catalyst.

Further, the conversion and selectivity mean the following.

Conversion: When compound (5) and a by-product having a 1-propenyl group ($—CH=CH—CH_3$) (comprising a cis-form and a trans form) are formed from compound (3), a value obtained by dividing the number of moles of the total of group (5) and the 1-propenyl group by the number of moles further including group (3), is represented as a numerical value by percentage.

Selectivity: A value obtained by dividing the number of moles of group (5) by the total number of moles of group (5) and the 1-propenyl group, is represented by a numerical value by percentage.

TABLE 1

| | Compound (3) | | | Compound (4) | | | Transition metal catalyst (C) | | | Compound (D) or Compound (Dα) | | Organic solvent (E) | |
|---|---|---|---|---|---|---|---|---|---|---|---|---|---|
| Ex. | Type | g | mmol | Type | g | mmol | Type | mg (solution) | μg (catalyst) | Type | mg | Type | g |
| 1 | 3-1 | 1.00 | 0.98 | 4-1 | 0.30 | 2.46 | C1 | 1.0 | 20 | — | — | E1 | 0.50 |
| 2 | 3-1 | 1.00 | 0.98 | 4-1 | 0.30 | 2.46 | C1 | 1.0 | 20 | DMSO | 1.0 | E1 | 0.50 |
| 3 | 3-1 | 1.00 | 0.98 | 4-1 | 0.30 | 2.46 | C1 | 1.0 | 20 | TMSO | 1.0 | E1 | 0.50 |
| 4 | 3-1 | 1.00 | 0.98 | 4-1 | 0.30 | 2.46 | C1 | 1.0 | 20 | Pyridine | 1.0 | E1 | 0.50 |
| 5 | 3-1 | 1.00 | 0.98 | 4-1 | 0.30 | 2.46 | C1 | 1.0 | 20 | Tetramethylurea | 1.0 | E1 | 0.50 |
| 6 | 3-1 | 1.00 | 0.98 | 4-1 | 0.30 | 2.46 | C1 | 1.0 | 20 | HMPA | 1.0 | E1 | 0.50 |
| 7 | 3-1 | 1.00 | 0.98 | 4-1 | 0.30 | 2.46 | C1 | 1.0 | 20 | DMF | 1.0 | E1 | 0.50 |
| 8 | 3-1 | 1.00 | 0.98 | 4-1 | 0.30 | 2.46 | C1 | 1.0 | 20 | Triethylamine | 1.0 | E1 | 0.50 |
| 9 | 3-1 | 1.00 | 0.98 | 4-1 | 0.30 | 2.46 | C1 | 1.0 | 20 | NMF | 1.0 | E1 | 0.50 |
| 10 | 3-1 | 1.00 | 0.98 | 4-1 | 0.30 | 2.46 | C1 | 1.0 | 20 | Acetone | 1.0 | E1 | 0.50 |
| 11 | 3-1 | 1.00 | 0.98 | 4-1 | 0.30 | 2.46 | C1 | 1.0 | 20 | THF | 1.0 | E1 | 0.50 |
| 12 | 3-1 | 1.00 | 0.98 | 4-1 | 0.30 | 2.46 | C1 | 1.0 | 20 | Toluene | 1.0 | E1 | 0.50 |
| 13 | 3-1 | 1.00 | 0.98 | 4-1 | 0.30 | 2.46 | C1 | 1.0 | 20 | Hexane | 1.0 | E1 | 0.50 |
| 14 | 3-1 | 1.00 | 0.98 | 4-1 | 0.30 | 2.46 | C1 | 1.0 | 10 | Methanol | 1.0 | E1 | 0.50 |
| 15 | 3-1 | 1.00 | 0.98 | 4-2 | 0.15 | 1.42 | C1 | 0.5 | 10 | — | — | E2 | 0.10 |
| 16 | 3-1 | 1.00 | 0.98 | 4-2 | 0.15 | 1.42 | C1 | 0.5 | 10 | DMSO | 2.0 | E2 | 0.10 |
| 17 | 3-1 | 1.00 | 0.98 | 4-3 | 1.20 | 4.99 | C1 | 0.5 | 10 | — | — | E2 | 0.10 |

TABLE 1-continued

| | | | | | | | | | | | | | | |
|---|---|---|---|---|---|---|---|---|---|---|---|---|---|---|
| 18 | 3-1 | 1.00 | 0.98 | 4-3 | 1.20 | 4.99 | C1 | 0.5 | 10 | DMSO | 2.0 | E2 | 0.10 |
| 19 | 3-1 | 1.00 | 0.98 | 4-1 | 0.30 | 2.46 | C2 | 1.1 | 20 | — | — | — | — |
| 20 | 3-1 | 1.00 | 0.98 | 4-1 | 0.30 | 2.46 | C2 | 1.1 | 20 | DMSO | 1.0 | — | — |

| | Reaction conditions | | Reaction results | |
|---|---|---|---|---|
| | | | Conversion | Selectivity |
| Ex. | Temp. | Hours | (%) | (%) |
| 1 | Room Temp. | 4 | 32 | 79 |
| 2 | Room Temp. | 4 | 100 | 96 |
| 3 | Room Temp. | 4 | 96 | 96 |
| 4 | Room Temp. | 4 | 84 | 92 |
| 5 | Room Temp. | 4 | 73 | 90 |
| 6 | Room Temp. | 4 | 48 | 90 |
| 7 | Room Temp. | 4 | 100 | 87 |
| 8 | Room Temp. | 4 | 83 | 86 |
| 9 | Room Temp. | 4 | 98 | 86 |
| 10 | Room Temp. | 4 | 71 | 77 |
| 11 | Room Temp. | 4 | 92 | 78 |
| 12 | Room Temp. | 4 | 94 | 80 |
| 13 | Room Temp. | 4 | 93 | 74 |
| 14 | Room Temp. | 4 | 90 | 65 |
| 15 | Room Temp. | 4 | 100 | 83 |
| 16 | Room Temp. | 4 | 83 | 96 |
| 17 | Room Temp. | 4 | 100 | 81 |
| 18 | Room Temp. | 4 | 100 | 95 |
| 19 | Room Temp. | 4 | 45 | 80 |
| 20 | Room Temp. | 4 | 100 | 96 |

TABLE 2

| | Compound (3) | | | Compound (4) | | | Transition metal catalyst (C) | | | Compound (D) | | Organic solvent (E) | |
|---|---|---|---|---|---|---|---|---|---|---|---|---|---|
| Ex. | Type | g | mmol | Type | g | mmol | Type | mg (solution) | μg (catalyst) | Type | mg | Type | g |
| 21 | 3-2 | 1.00 | 0.21 | 4-1 | 0.06 | 0.49 | C1 | 1.0 | 20 | — | — | E1 | 0.50 |
| 22 | 3-2 | 1.00 | 0.21 | 4-1 | 0.06 | 0.49 | C1 | 1.0 | 20 | DMSO | 1.0 | E1 | 0.50 |
| 23 | 3-3 | 1.00 | 0.24 | 4-1 | 0.10 | 0.82 | C1 | 1.0 | 20 | — | — | E1 | 0.50 |
| 24 | 3-3 | 1.00 | 0.24 | 4-1 | 0.10 | 0.82 | C1 | 1.0 | 20 | DMSO | 1.0 | E1 | 0.50 |
| 25 | 3-4 | 1.00 | 0.23 | 4-1 | 0.05 | 0.41 | C1 | 1.0 | 20 | — | — | E1 | 0.50 |
| 26 | 3-4 | 1.00 | 0.23 | 4-1 | 0.05 | 0.41 | C1 | 1.0 | 20 | DMSO | 1.0 | E1 | 0.50 |
| 27 | 3-5 | 1.00 | 0.23 | 4-1 | 0.05 | 0.41 | C1 | 1.0 | 20 | — | — | E1 | 0.50 |
| 28 | 3-5 | 1.00 | 0.23 | 4-1 | 0.05 | 0.41 | C1 | 1.0 | 20 | DMSO | 1.0 | E1 | 0.50 |
| 29 | 3-6 | 1.00 | 0.23 | 4-1 | 0.05 | 0.41 | C1 | 1.0 | 20 | — | — | E1 | 0.50 |
| 30 | 3-6 | 1.00 | 0.23 | 4-1 | 0.05 | 0.41 | C1 | 1.0 | 20 | DMSO | 1.0 | E1 | 0.50 |
| 31 | 3-7 | 0.50 | 4.4 | 4-1 | 0.64 | 5.25 | C1 | 1.2 | 24 | — | — | — | — |
| 32 | 3-7 | 0.50 | 4.4 | 4-1 | 0.64 | 5.25 | C1 | 1.2 | 24 | DMSO | 1.0 | — | — |
| 33 | 3-7 | 0.50 | 4.4 | 4-1 | 0.64 | 5.25 | C1 | 1.2 | 24 | TMSO | 1.0 | — | — |
| 34 | 3-8 | 0.50 | 4.4 | 4-1 | 0.64 | 5.25 | C1 | 1.2 | 24 | — | — | — | — |
| 35 | 3-8 | 0.50 | 4.4 | 4-1 | 0.64 | 5.25 | C1 | 1.2 | 24 | DMSO | 1.0 | — | — |
| 36 | 3-8 | 0.50 | 4.4 | 4-1 | 0.64 | 5.25 | C1 | 1.2 | 24 | TMSO | 1.0 | — | — |
| 37 | 3-9 | 0.50 | 0.98 | 4-1 | 0.14 | 1.15 | C1 | 0.5 | 10 | — | — | — | — |
| 38 | 3-9 | 0.50 | 0.98 | 4-1 | 0.14 | 1.15 | C1 | 0.5 | 10 | DMSO | 0.5 | — | — |
| 39 | 3-9 | 0.5 | 0.98 | 4-1 | 0.14 | 1.15 | C1 | 0.5 | 10 | TMSO | 0.5 | — | — |
| 40 | 3-10 | 0.50 | 0.93 | 4-1 | 0.13 | 1.07 | C1 | 0.5 | 10 | — | — | — | — |
| 41 | 3-10 | 0.50 | 0.93 | 4-1 | 0.13 | 1.07 | C1 | 0.5 | 10 | DMSO | 0.5 | — | — |
| 42 | 3-10 | 0.50 | 0.93 | 4-1 | 0.13 | 1.07 | C1 | 0.5 | 10 | TMSO | 0.5 | — | — |
| 43 | 3-11 | 0.50 | 0.17 | 4-1 | 0.03 | 0.25 | C1 | 1.0 | 20 | — | — | E3 | 0.30 |
| 44 | 3-11 | 0.50 | 0.17 | 4-1 | 0.03 | 0.25 | C1 | 1.0 | 20 | DMSO | 2.0 | E3 | 0.30 |
| 45 | 3-11 | 0.50 | 0.17 | 4-1 | 0.03 | 0.25 | C1 | 1.0 | 20 | TMSO | 2.0 | E3 | 0.30 |
| 46 | 3-12 | 0.50 | 4.5 | 4-1 | 0.65 | 5.33 | C1 | 1.0 | 20 | — | — | — | — |
| 47 | 3-12 | 0.50 | 4.5 | 4-1 | 0.65 | 5.33 | C1 | 1.0 | 20 | DMSO | 1.0 | — | — |
| 48 | 3-12 | 0.50 | 4.5 | 4-1 | 0.65 | 5.33 | C1 | 1.0 | 20 | TMSO | 1.0 | — | — |

| | Reaction conditions | | Reaction results | |
|---|---|---|---|---|
| | | | Conversion | Selectivity |
| Ex. | Temp. | Hours | (%) | (%) |
| 21 | Room Temp. | 4 | 36 | 80 |
| 22 | Room Temp. | 4 | 98 | 97 |
| 23 | Room Temp. | 4 | 29 | 79 |

TABLE 2-continued

| | | | | |
|---|---|---|---|---|
| 24 | Room Temp. | 4 | 100 | 96 |
| 25 | Room Temp. | 4 | 20 | 80 |
| 26 | Room Temp. | 4 | 100 | 95 |
| 27 | Room Temp. | 4 | 42 | 80 |
| 28 | Room Temp. | 4 | 100 | 96 |
| 29 | Room Temp. | 4 | 26 | 82 |
| 30 | Room Temp. | 4 | 99 | 96 |
| 31 | Room Temp. | 4 | 94 | 82 |
| 32 | Room Temp. | 4 | 100 | 93 |
| 33 | Room Temp. | 4 | 100 | 94 |
| 34 | Room Temp. | 4 | 88 | 81 |
| 35 | Room Temp. | 4 | 100 | 95 |
| 36 | Room Temp. | 4 | 100 | 95 |
| 37 | Room Temp. | 4 | 74 | 80 |
| 38 | Room Temp. | 4 | 98 | 95 |
| 39 | Room Temp. | 4 | 100 | 96 |
| 40 | Room Temp. | 4 | 85 | 81 |
| 41 | Room Temp. | 4 | 100 | 96 |
| 42 | Room Temp. | 4 | 100 | 95 |
| 43 | Room Temp. | 4 | 100 | 79 |
| 44 | Room Temp. | 4 | 100 | 94 |
| 45 | Room Temp. | 4 | 100 | 96 |
| 46 | Room Temp. | 4 | 40 | 79 |
| 47 | Room Temp. | 4 | 65 | 97 |
| 48 | Room Temp. | 4 | 69 | 96 |

In Ex. 2, 3, 16, 18, 20, 22, 24, 26, 28, 30, 32, 33, 35, 36, 38, 39, 41, 42, 44, 45, 47 and 48, compounds having group (5) were obtained with high selectivity.

INDUSTRIAL APPLICABILITY

According to the production method of the present invention, a silicon compound useful for surface treatment to impart water/oil repellency to the surface of a substrate such as a member constituting a surface of a touch panel to be touched by a finger, can be produced with high selectivity by a simple and easy method.

What is claimed is:

1. A method for producing a silicon compound, comprising reacting a compound having a group represented by formula (3) and a silicon compound (4) having an H—Si bond in the presence of a transition metal catalyst (C) and dimethyl sulfoxide or tetramethylene sulfoxide to obtain a compound having a group represented by formula (5):

—CH$_2$CH=CH$_2$ (3)

—CH$_2$CH$_2$CH$_2$Si≡ (5).

2. The method according to claim 1, wherein the silicon compound (4) having an H—Si bond is a compound represented by formula (41), and the group represented by the formula (5) is a group represented by formula (5-1):

HSiL$_m$R$_n$ (41)

—CH$_2$CH$_2$CH$_2$SiL$_m$R$_n$ (5-1)

wherein L a hydrolyzable group, R is a monovalent hydrocarbon group, m is an integer of from 1 to 3, and n is an integer of from 0 to 2, provided m+n=3.

3. The method according to claim 2, wherein L is a C$_{1-4}$ alkoxy group.

4. The method according to claim 1, wherein the silicon compound (4) having an H—Si bond is a linear or cyclic organopolysiloxane compound.

5. The method according to claim 1, wherein the compound having a group represented by the formula (3) is a compound having an allyloxy group.

6. The method according to claim 1, wherein the compound having a group represented by the formula (3) is a compound having from 1 to 3 groups represented by the formula (3).

7. The method according to claim 1, wherein the compound having a group represented by the formula (3) is a compound having a polyoxyalkylene chain or a polyoxyfluoroalkylene chain.

8. The method according to claim 1, wherein the number average molecular weight of the compound having a group represented by the formula (3) is from 200 to 20,000.

9. The method according to claim 1, wherein the transition metal catalyst (C) is a platinum catalyst.

10. The method according to claim 9, wherein the transition metal catalyst (C) is a Pt/divinyltetramethyldisiloxane complex or a Pt/tetramethyltetravinylcyclotetrasiloxane complex.

11. The method according to claim 1, wherein the compound having a group represented by the formula (3) is a compound represented by formula (3A), a compound represented by formula (3B), or a compound represented by formula (3C):

R$^A$—CH$_2$CH=CH$_2$ (3A)

CH$_2$=CHCH$_2$—R$^B$—CH$_2$CH=CH$_2$ (3B)

$$\text{CH}_2=\text{CHCH}_2-\underset{\underset{\text{CH}_2\text{CH}=\text{CH}_2}{|}}{\text{R}^C}-\text{CH}_2\text{CH}=\text{CH}_2 \quad (3C)$$

wherein each of R$^A$ and R$^B$ is an organic group having a polyoxyalkylene chain or a polyoxyfluoroalkylene chain, and R$^C$ is a trivalent organic group.

12. The method according to claim 1, wherein the compound having a group represented by the formula (3) is a compound represented by formula (3A) or a compound represented by formula (3B):

R$^A$—CH$_2$CH=CH$_2$ (3A)

CH$_2$=CHCH$_2$—R$^B$—CH$_2$CH=CH$_2$ (3B)

wherein each of $R^A$ and $R^B$ is an organic group having a polyoxyfluoroalkylene chain.

13. The method according to claim 1, wherein the compound having a group represented by the formula (3) is a compound represented by formula (3A):

$$R^A-CH_2CH=CH_2 \quad (3A)$$

wherein $R^A$ is $CH_3-R^{A1}-O-$, $CH_3-R^{A1}-O-(C_yH_{2y}O)_{y1}-$, $CH_3-R^{A1}-$, $CF_3-R^{A1}-O-$, $CF_3-R^{A1}-O-(C_yH_{2y}O)_{y1}-$, $CF_3-R^{A1}-O-(C_oF_{2o}O)_{o1}-$, $CF_3-R^{A1}-$, A-O-Q-$(C_bF_{2b}O)_d$—X—O—, or a group represented by any one of following formulae:

$$\underset{O}{\underset{\diagdown\diagup}{CH_2CH}}-R^{A1}-O- \qquad \underset{O}{\underset{\diagdown\diagup}{CF_2CF}}-R^{A1}-O-,$$

wherein:
- $R^{A1}$ is a single bond, a $C_{1-30}$ alkylene group, or a $C_{1-30}$ fluoroalkylene group, and the number of carbon atoms in the alkylene group or the fluoroalkylene group is 1 to 20;
- each of y and o is independently an integer of from 1 to 10;
- each of y1 and o1 is independently an integer of from 1 to 500;
- A is a $C_{1-20}$ perfluoroalkyl group;
- Q is a single bond, —$CH_2$—, —CH—, -$Q^1$-$CH_2$—, -$Q^1$-CHF—, -$Q^1$-O—$CH_2$—, -$Q^1$-O—CHF—, -$Q^1CH_2$—O— or -$Q^1$-CHF—O—;
- $Q^1$ is a $C_{1-10}$ fluoroalkylene group, a group in which an etheric oxygen atom is inserted between two carbon atoms of a $C_{2-10}$ fluoroalkylene group, a $C_{1-10}$ alkylene group, or a group in which an etheric oxygen atom is inserted between two carbon atoms of a $C_{2-10}$ alkylene group;
- b is an integer of from 1 to 10;
- d is an integer of from 1 to 200, provided that when d is at least 2, $(C_bF_{2b}O)_d$ is optionally composed of at least two kinds of $C_bF_{2b}O$ different in b; and
- X is a divalent organic group having no $CF_2O$.

14. The method according to claim 1, wherein the compound having a group represented by the formula (3) is a compound represented by formula (3B):

$$CH_2=CHCH_2-R^B-CH_2CH=CH_2 \quad (3B)$$

wherein:
- $R^B$ is a single bond, —O—, —O—$R^{B1}$—O—, —O—$(C_yH_{2y}O)_{y1}$—, —O—$R^{B1}$, —O—$(C_yH_{2y}O)_{y1}$—, $R^{B1}$, —$R^{B1}$—O—, —O—$R^{B1}$—, —$R^{B1}$—O—$(C_yH_{2y}O)_{y1}$—, or —O-Q-$(C_bF_{2b}O)_d$—X—O—;
- $R^{B1}$ is a $C_{1-30}$ alkylene group, or a $C_{1-30}$ fluoroalkylene group, and the number of carbon atoms in the alkylene group or the fluoroalkylene group is 1 to 20;
- y is an integer of from 1 to 10;
- y1 is an integer of from 1 to 500;
- Q is a single bond,
- Q is a single bond, —$CH_2$—, —CHF—, -$Q^1$-$CH_2$—, -$Q^1$-CHF—, -$Q^1$-O—$CH_2$—, -$Q^1$-O—CHF—, -$Q^1CH_2$—O— or -$Q^1$-CHF—O—;
- $Q^1$ is a $C_{1-10}$ fluoroalkylene group, a group in which an etheric oxygen atom is inserted between two carbon atoms of a $C_{2-10}$ fluoroalkylene group, a $C_{1-10}$ alkylene group, or a group in which an etheric oxygen atom is inserted between two carbon atoms of a $C_{2-10}$ alkylene group;
- b is an integer of from 1 to 10;
- d is an integer of from 1 to 200, provided that when d is at least 2, $(C_bF_{2b}O)_d$ is optionally composed of at least two kinds of $C_bF_{2b}O$ different in b; and
- X is a divalent organic group having no $CF_2O$.

15. The method according to claim 1, wherein a selectivity of the reaction to obtain the compound having the group represented by formula (5) is 95% or more.

* * * * *